United States Patent
Prakash et al.

(10) Patent No.: US 12,102,508 B2
(45) Date of Patent: *Oct. 1, 2024

(54) ANTIMICROBIAL WOUND CARE DRESSING

(71) Applicant: OHIO STATE INNOVATION FOUNDATION, Columbus, OH (US)

(72) Inventors: Shaurya Prakash, Columbus, OH (US); Vishwanath V. Subramaniam, Westerville, OH (US); Molly Marie Bennett, Seattle, WA (US); Chandan K. Sen, Upper Arlington, OH (US); Travis Hamilton Jones, Columbus, OH (US); Emily Quinn Rosenthal, Dublin, OH (US); Shomita Steiner, Olean, NY (US); Sashwati Roy, Upper Arlington, OH (US); Joseph Dean West, Richwood, OH (US); Piya Das Ghatak, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 1500 days.

This patent is subject to a terminal disclaimer.

(21) Appl. No.: 16/343,214

(22) PCT Filed: Oct. 20, 2017

(86) PCT No.: PCT/US2017/057597
§ 371 (c)(1),
(2) Date: Apr. 18, 2019

(87) PCT Pub. No.: WO2018/075893
PCT Pub. Date: Apr. 26, 2018

(65) Prior Publication Data
US 2019/0247234 A1 Aug. 15, 2019

Related U.S. Application Data

(60) Provisional application No. 62/411,089, filed on Oct. 21, 2016.

(51) Int. Cl.
*A61F 13/01* (2024.01)
*A61F 13/00* (2024.01)
(Continued)

(52) U.S. Cl.
CPC .. *A61F 13/01008* (2024.01); *A61F 13/00051* (2013.01); *A61F 13/05* (2024.01);
(Continued)

(58) Field of Classification Search
None
See application file for complete search history.

(56) References Cited

U.S. PATENT DOCUMENTS 5,203,768 A * 4/1993 Haak ............ A61N 1/0448
604/20
9,387,125 B1 * 7/2016 Duda ............ A61N 1/0468
(Continued)

FOREIGN PATENT DOCUMENTS

GB 2434544 A 8/2007
WO 02098502 A2 12/2002
(Continued)

OTHER PUBLICATIONS

European Extended Search Report issued for Application No. 18760876.5, dated Nov. 12, 2020.
(Continued)

*Primary Examiner* — Carl H Layno
*Assistant Examiner* — Manolis Pahakis
(74) *Attorney, Agent, or Firm* — Meunier Carlin & Curfman LLC

(57) ABSTRACT

Antimicrobial dressings for prevention and mitigation of biofilm and bacterial infection by an applied electric current
(Continued)

are provided. Methods of making the dressings and methods of applying an electric current to promote the wound healing process are also disclosed.

6 Claims, 20 Drawing Sheets

(51) Int. Cl.
  *A61F 13/05* (2024.01)
  *A61N 1/04* (2006.01)
  *A61N 1/08* (2006.01)
  *A61N 1/20* (2006.01)
  *A61N 1/32* (2006.01)

(52) U.S. Cl.
  CPC ......... *A61N 1/0468* (2013.01); *A61N 1/0484* (2013.01); *A61N 1/08* (2013.01); *A61N 1/205* (2013.01); *A61N 1/32* (2013.01); *A61F 2013/00238* (2013.01); *A61F 2013/00297* (2013.01)

(56) References Cited

U.S. PATENT DOCUMENTS

| | | | |
|---|---|---|---|
| 11,786,727 B2* | 10/2023 | Colborn | A61N 1/3603 607/59 |
| 2004/0142227 A1* | 7/2004 | Sugai | H01M 8/0271 429/457 |
| 2005/0004509 A1* | 1/2005 | Sun | A61N 1/0428 977/932 |
| 2005/0004550 A1 | 1/2005 | Sun et al. | |
| 2005/0085751 A1* | 4/2005 | Daskal | A61N 1/326 602/2 |
| 2006/0015052 A1* | 1/2006 | Crisp | A61F 13/00063 602/41 |
| 2007/0048601 A1* | 3/2007 | Wu | H01M 4/42 429/231.95 |
| 2007/0060862 A1 | 3/2007 | Sun et al. | |
| 2008/0097564 A1* | 4/2008 | Lathrop | A61N 1/321 607/145 |
| 2009/0062723 A1 | 3/2009 | Skiba | |
| 2010/0069813 A1* | 3/2010 | Crisp | A61F 13/00021 602/46 |
| 2010/0204752 A1 | 8/2010 | Tremblay et al. | |
| 2011/0015697 A1 | 1/2011 | McAdams | |
| 2011/0070506 A1* | 3/2011 | Friesen | H01M 8/184 429/417 |
| 2011/0077736 A1* | 3/2011 | Rofougaran | A61M 31/002 623/8 |
| 2011/0112465 A1 | 5/2011 | Anderson et al. | |
| 2011/0118655 A1* | 5/2011 | Fassih | A61N 1/205 604/20 |
| 2011/0271424 A1 | 11/2011 | Revol Cavalier | |
| 2013/0095138 A1 | 4/2013 | Norton et al. | |
| 2015/0126834 A1 | 5/2015 | Wang et al. | |
| 2015/0155596 A1* | 6/2015 | Gardner | H01M 50/581 429/149 |
| 2015/0311746 A1* | 10/2015 | Friesen | H01M 10/4242 320/128 |
| 2015/0374984 A1 | 12/2015 | King et al. | |
| 2015/0376599 A1* | 12/2015 | Subramaniam | C12N 13/00 435/283.1 |
| 2016/0059009 A1* | 3/2016 | Skiba | A61M 1/90 604/23 |
| 2016/0081580 A1 | 3/2016 | Bergelin et al. | |
| 2016/0141623 A1* | 5/2016 | Yoon | H01M 4/62 156/60 |
| 2016/0287868 A1* | 10/2016 | Bogie | A61N 1/36031 |
| 2017/0020736 A1* | 1/2017 | Davis | A61F 13/00072 |
| 2017/0025720 A1* | 1/2017 | Kaiser | H01M 10/425 |
| 2017/0062840 A1* | 3/2017 | Wu | H01M 4/466 |
| 2017/0222288 A1* | 8/2017 | Ashfield | H01M 12/06 |
| 2017/0229704 A1 | 8/2017 | Takahashi et al. | |
| 2018/0147404 A1* | 5/2018 | Nagel | A61N 1/0456 |
| 2018/0243550 A1* | 8/2018 | Paluszcyk | A61N 1/0492 |
| 2018/0294391 A1* | 10/2018 | Emura | H01L 33/647 |
| 2018/0331363 A1* | 11/2018 | Winsberg | H01M 8/188 |
| 2019/0117955 A1* | 4/2019 | Nagel | A61N 1/36003 |
| 2019/0117958 A1* | 4/2019 | Paluszcyk | A61N 1/0428 |
| 2019/0151647 A1 | 5/2019 | Kay et al. | |
| 2019/0247234 A1 | 8/2019 | Prakash et al. | |
| 2020/0388867 A1* | 12/2020 | Kim | H01M 8/04201 |
| 2023/0166101 A1* | 6/2023 | Prakash | A61N 1/0468 607/149 |

FOREIGN PATENT DOCUMENTS

| | | |
|---|---|---|
| WO | 2007088348 | 12/2007 |
| WO | 2014188070 | 11/2014 |
| WO | 2016021684 A1 | 2/2016 |
| WO | 2016044341 | 3/2016 |
| WO | 2016100307 A1 | 6/2016 |
| WO | 2018020725 A1 | 1/2018 |

OTHER PUBLICATIONS

H. Elayan, R.M. Shubair, and A. Kiourti, "Wireless sensors for medical applications: Current status and future challenges," in Proc. Europ. Conf. Antennas Propag., Mar. 2017.
He, B., Baird, R., Datta, A., George, S., Hecht, B., et al.: 'Grand challenges in interfacing engineering with life sciences and medicine', IEEE Trans. Biomed. Eng., vol. 60, No. 3, pp. 589-598, 2013.
International Data Corporation (IDC), Press Release, Mar. 17, 2016. https://www.idc.com/getdoc.jsp?containerId=prUS41100116.
Islam, A., Kiourti, A., Volakis, J.L.: 'A novel method of deep tissue biomedical imaging using a wearable sensor', IEEE Sensors J., 2016, 26, (1), pp. 265-270.
Jost, K., Dion, G., Gogotsi, Y.: 'Textile energy storage in perspective', J. Mater. Chem., 2014, 28, (2), pp. 10776-10787.
Lee, Y.H., Kim, J.S., Noh, J., Lee, I., Kim, H.J., Choi, S., Seo, J., Jeon, S., Kim, T.S., Lee, J.Y., Choi, J.W.: 'Wearable textile battery rechargeable by solar energy', Nano Letters, 2013, 13, (11), pp. 5753-5761.
M.A. Hannan, S. Mutashar, S.A. Samad, and A. Hussain, "Energy harvesting for the implantable biomedical devices: issues and challenges," Biomed. Eng. Online, vol. 13, 2014.
Metcalf, D., Milliard, S.T.J., Gomez, M., Schwartz, M.: 'Wearables and the Internet of Things for health: wearable, interconnected devices promise more efficient and comprehensive health care', IEEE Pulse, 2016, 7, (5), pp. 35-39.
Mukhopadhyay, S.C.: 'Wearable sensors for human activity monitoring: a review', IEEE Sensors J., 2015, 15, (3), pp. 1321-1330.
Olgun, U., Chen, C.C., Volakis, J.L.: 'Investigation of rectenna array configurations for RF power harvesting', IEEE Antennas Wireless Propag. Lett., 2011, 10, pp. 262-265.
Syscom Advanced Materials, Amberstrand fiber. 2015. https://www.metalcladfibers.com/amberstrand/.
Vomaris: 'Procellera: Wound care with advanced microcurrent technology', http://procellera.com/, accessed Nov. 2016, 6 pages.
Zheng, Y.-L., Ding, X.-R., Poon, C.C.Y., Lo, B.P.L., Zhang, H., Zhou, X.-L., Yang, G.-Z., Zhao, N., Zhang, Y.-T.: 'Unobtrusive sensing and wearable devices for health informatics', IEEE Trans. Biomed. Eng., 2014, 61, (5), pp. 1538-1554.
U.S. Patent and Trademark Office. Final Office Action. Issued in U.S. Appl. No. 16/490,789 on Nov. 19, 2021. 18 pages.
European Extended Search Report issued for Application No. 17861317, dated May 4, 2020.
International Search Report and Written Opinion. Issued by the US International Searching Authority. Application No. PCT/US2017/057597. Jan. 5, 2018. 9 pages.
Klasson, David H. "Treatment of Chronic Venous Leg Ulcers With Raw Silk." Angiology 17.6 (1966): 369-376.
International Preliminary Report on Patentability issued by the International Bureau of WIPO in PCT Application No. PCT/US2018/020725 on Sep. 12, 2019. 6 pages.

(56) References Cited

OTHER PUBLICATIONS

Hurlow et al., Clinical Biofilms: A Challenging Frontier in Wound Care. Adv. Wound Care, 2015, 4(5): 295-301.
Banerjee, et al., Improvement of Human Keratinocyte Migration by a Redox Active Bioelectric Dressing. PLoS One 2014, 9:3, e89239.
Costerton, J. W., Stewart, P. S., & Greenberg, E. P. (1999). Bacterial Biofilms: A Common Cause of Persistent Infections. Science, 284(5418), 1318-1322. doi: 10.1126/science.284.5418.1318.
Sandvik, E. L., McLeod, B. R., Parker, A. E., & Stewart, P. S. (2013). Direct electric current treatment under physiologic saline conditions kills *Staphylococcus epidermidis* biofilms via electrolytic generation of hypochlorous acid. PLoS One, 8(2), e55118. doi: 10.1371/journal.pone.0055118.
International Preliminary Report on Patentability issued for Application No. PCT/US2017/057597, dated May 2, 2019, 7 pages.
International Search report and Written Opinion issued for Application No. PCT/US2018/020725, dated May 16, 2018, 8 pages.
Bennett, Molly Abstract for "Design, Fabrication, and Characterization of Electroceutical Bandages for Treatment of Chronically Infected Wounds." Electronic Thesis or Dissertation. Ohio State University, Sep. 30, 2016. https://etd.ohiolink.edu/ (This is a publication by one of the inventors that occurred less than one year before the effective filing date of the present application and thus is not prior art to the present application, but is submitted to provide the Examiner with an idea of the state of the art at the time of the invention.).
International Search Report and Written Opinion issued for Application No. PCT/US2021/026414, dated Aug. 31, 2021.
Kiamco, Mia Mae, et al. "Hypochlorous-acid-generating electrochemical scaffold for treatment of wound biofilms." Scientific reports 9.1 (2019): 1-13.
Arenschield, I., "Electrifying wound care: Better bandages to destroy bacteria", Retrieved on Jun. 16, 2021.https://news.bsu.edu/electrifying-wound-care-better-bandages-to-destroy-bacteria/.
Dusane, Devendra H., et al. "Electroceutical treatment of Pseudomonas aeruginosa biofilms." Scientific reports (2019) 9:2008. Retreived on Jun. 16, 2021. https://www.nature.com/articles/s41598-018-37891-y.
Office Action issued for U.S. Appl. No. 16/490,789, dated Aug. 6, 2021.
Antonov, Dimitar et al. "Methods for the assessment of barrier function." Skin Barrier Function 49 (2016): 61-70.
Bai, Huai et al. "DC electric stimulation upregulates angiogenic factors in endothelial cells through activation of VEGF receptors." Cytokine 55.1 (2011): 110-115.
Bai, Huai, et al. "DC electric fields induce distinct preangiogenic responses in microvascular and macrovascular cells." Arteriosclerosis, thrombosis, and vascular biology 24.7 (2004): 1234-1239.
Bogie, Kath M., et al. "Electrical stimulation for pressure sore prevention and wound healing." Assistive Technology 12.1 (2000): 50-66.
Eming, Sabine A. et al. "Inflammation and metabolism in tissue repair and regeneration." Science 356.6342 (2017): 1026-1030.
Fleischli, John G. et al. "Electrical stimulation in wound healing." The Journal of Foot and Ankle Surgery 36.6 (1997): 457-461.
Hackam, David J. et al. "Cellular, biochemical, and clinical aspects of wound healing." Surgical infections 3.S1 (2002): s23-s35.
Jones, T. H., et al. "Design and characterization of an electromagnetic probe for distinguishing morphological differences in soft tissues." Review of Scientific Instruments 89.8 (2018).
Li, Xuefeng et al. "Effects of direct current electric fields on cell migration and actin filament distribution in bovine vascular endothelial cells." Journal of vascular research 39.5 (2002): 391-404.
Lin, Francis, et al. "Lymphocyte electrotaxis in vitro and in vivo." The Journal of Immunology 181.4 (2008): 2465-2471.
Prakash, S., et al. "Ex vivo electrical impedance measurements on excised hepatic tissue from human patients with metastatic colorectal cancer." Physiological measurement 36.2 (2015): 315.
Prakash, Shaurya et al. "Theory, fabrication and applications of microfluidic and nanofluidic biosensors." Philosophical Transactions of the Royal Society A: Mathematical, Physical and Engineering Sciences 370.1967 (2012): 2269-2303.
Rayner, Benjamin S., et al. "Role of hypochlorous acid (HOCl) and other inflammatory mediators in the induction of macrophage extracellular trap formation." Free Radical Biology and Medicine 129 (2018): 25-34.
Rose, Lloyd F. et al. "The burn wound microenvironment." Advances in wound care 5.3 (2016): 106-118.
Roy, Sashwati, et al. "Disposable patterned electroceutical dressing (PED-10) is safe for treatment of open clinical chronic wounds." Advances in wound care 8.4 (2019): 149-159.
Roy, Sashwati, et al. "Mixed-species biofilm compromises wound healing by disrupting epidermal barrier function." The Journal of pathology 233.4 (2014): 331-343.
Vilkhu, Ramandeep, et al. "Power generation for wearable electronics: Designing electrochemical storage on fabrics." IEEE Access 6 (2018): 28945-28950.
Zhao, Min, et al. "Electric field-directed cell motility involves up-regulated expression and asymmetric redistribution of the epidermal growth factor receptors and is enhanced by fibronectin and laminin." Molecular biology of the cell 10.4 (1999): 1259-1276.
Zhao, Min, et al. "Electrical signals control wound healing through phosphatidylinositol-3-OH kinase-γ and PTEN." Nature 442.7101 (2006): 457-460.
Zhao, Min, et al. "Electrical stimulation directly induces pre-angiogenic responses in vascular endothelial cells by signaling through VEGF receptors." Journal of cell science 117.3 (2004): 397-405.
Zhao, Min, et al. "Membrane lipids, EGF receptors, and intracellular signals colocalize and are polarized in epithelial cells moving directionally in a physiological electric field." The FASEB Journal 16.8 (2002): 857-859.
European Patent Office. Extended European search report. Issued in Application No. EP 21783902.6 on Mar. 21, 2024. 7 pages.

\* cited by examiner

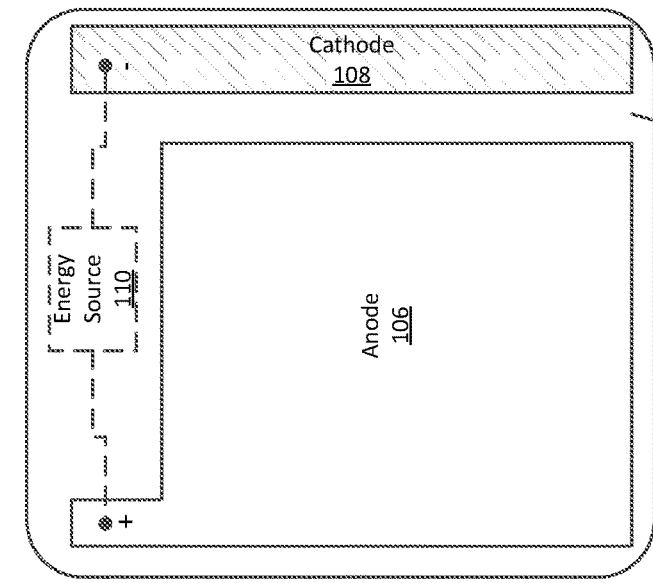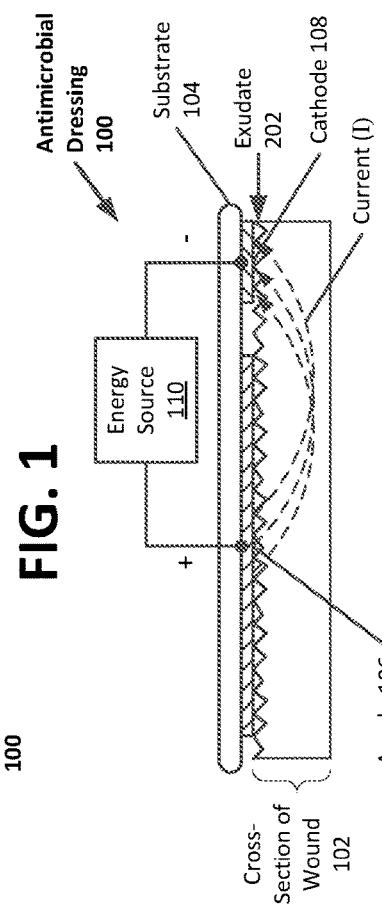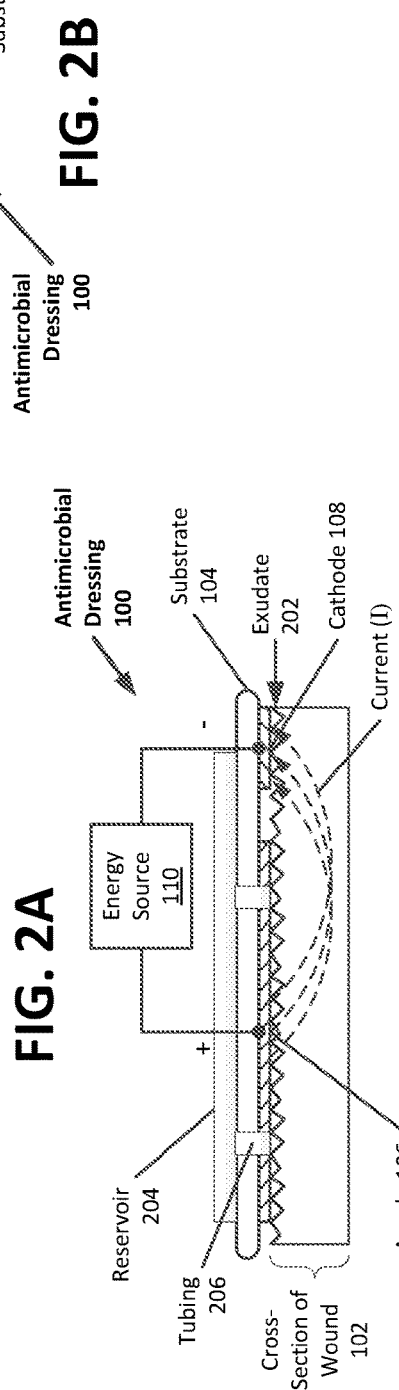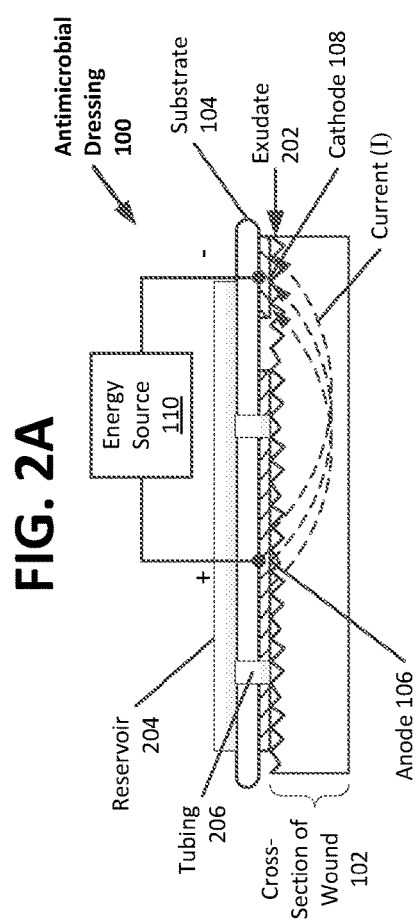

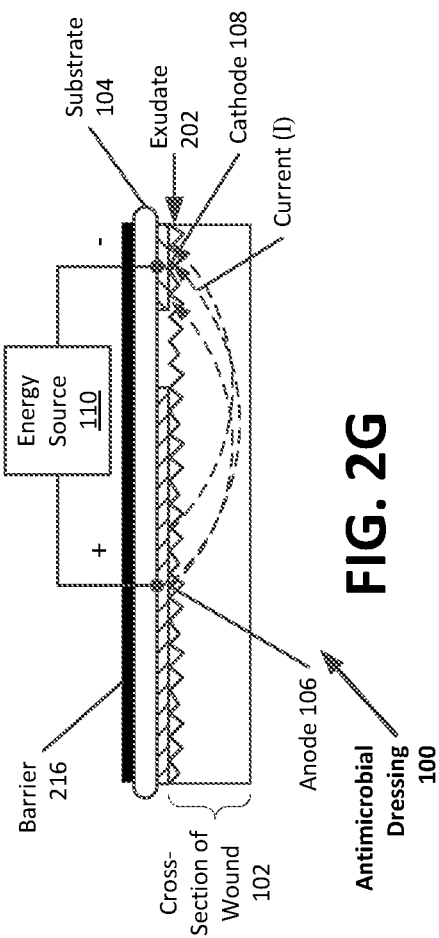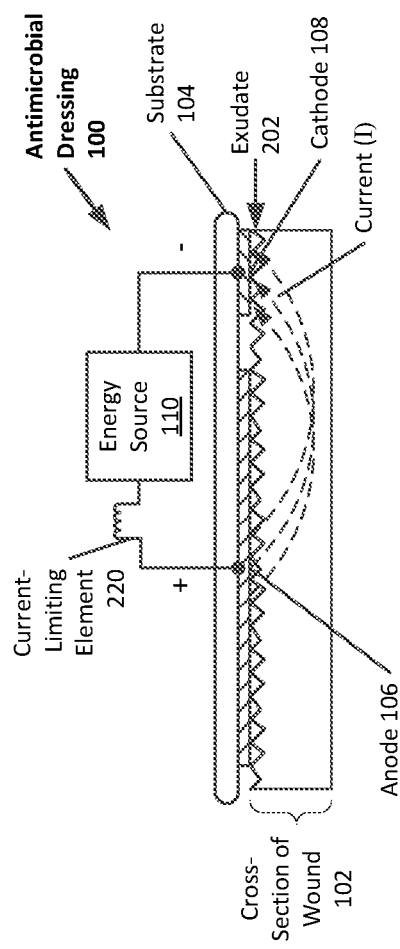

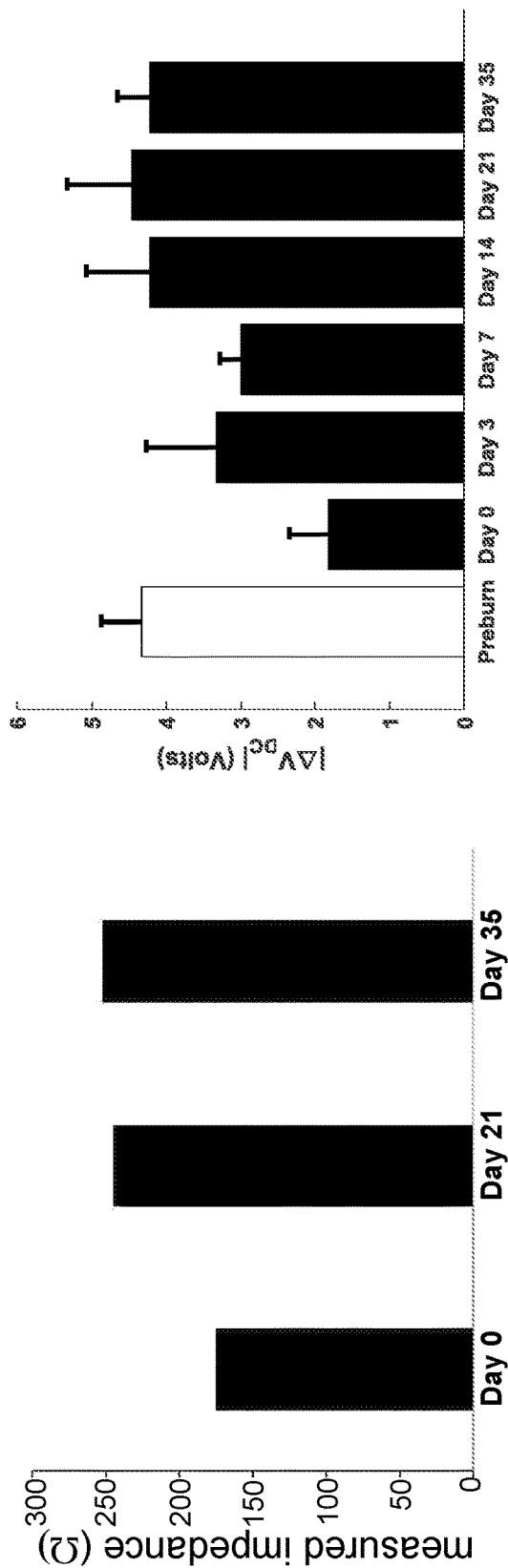
FIG. 2I
FIG. 2J
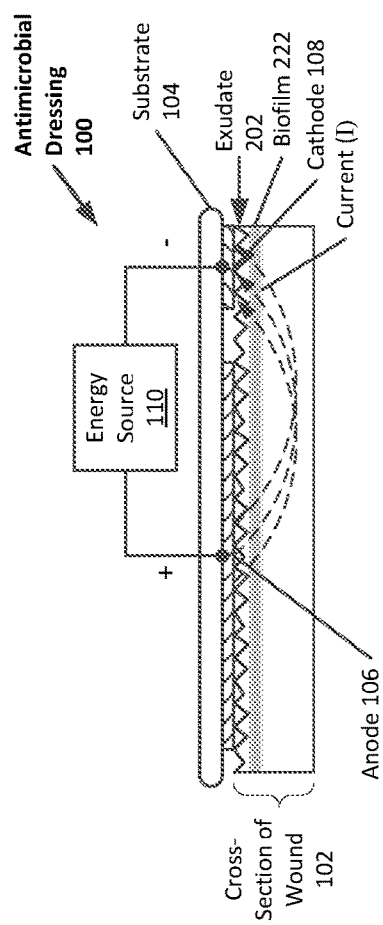
FIG. 2K

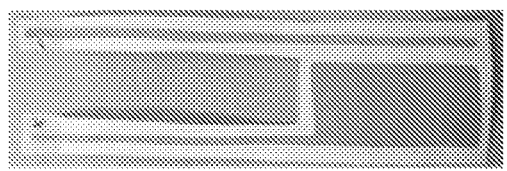
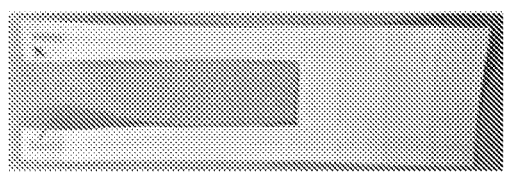
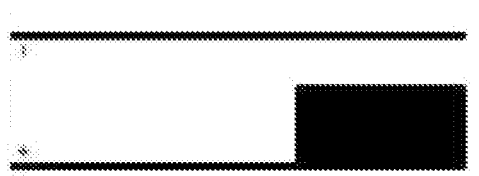
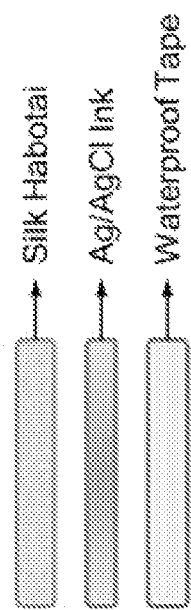
FIG. 5C
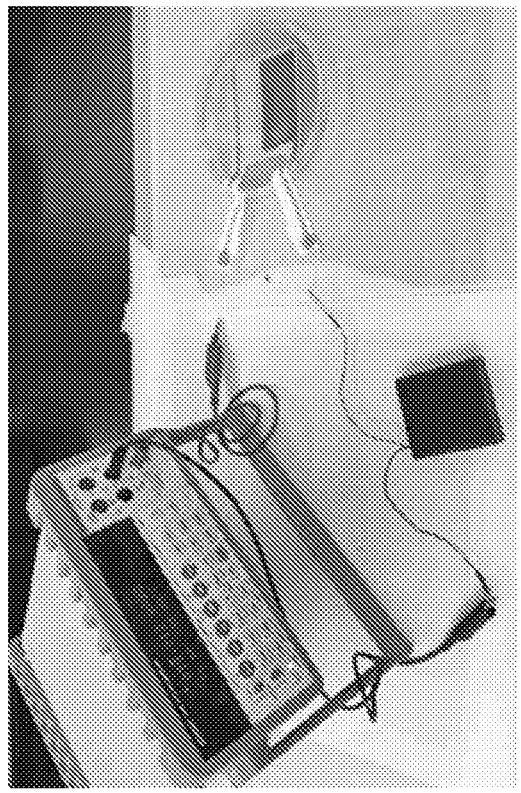
FIG. 6

ANTIMICROBIAL WOUND CARE DRESSING

CROSS-REFERENCE TO RELATED APPLICATION

This application is a national stage application filed under 35 U.S.C. § 371 of PCT/US2017/057597 filed Oct. 20, 2017, which claims priority to and benefit of U.S. Provisional patent application Ser. No. 62/411,089 filed Oct. 21, 2016, which is fully incorporated by reference and made a part hereof.

STATEMENT OF GOVERNMENT SUPPORT

This invention was made with government support under Grant No. TR001070, awarded by the National Institutes of Health (NIH). The government has certain rights in the invention.

TECHNICAL FIELD

The present disclosure is generally directed to devices and methods for generating and directing an electric current through a wound to promote healing. More specifically, the present disclosure is directed to devices that include dressings for applying an electric current through a wound, which can provide antimicrobial and antibiofilm effects and facilitate wound healing.

BACKGROUND

There are two kinds of bacterial strains, (i) free-floating or planktonic and (ii) attached or sessile bacteria. Surface attachment provides additional protection for the bacteria, improves cell-cell interactions (quorum sensing), and help concentrate nutrients. A biofilm is a form of sessile bacteria, consisting of a dense colony of bacteria attached to a surface. A bacterial biofilm is defined as "a structured community of bacterial cells enclosed in a self-produced polymeric matrix and adherent to an inert or living surface," (Costerton, J. W., Stewart, P. S., & Greenberg, E. P. (1999). Bacterial Biofilms: A Common Cause of Persistent Infections. Science, 284(5418), 1318-1322. doi: 10.1126/science.284.5418.1318). The polymeric matrix is connected with strong chemical bonds, resistant and highly adaptable to biocides, antibiotics, and physical stress. Examples of physical stress and other environmental conditions include extreme temperatures, pH changes, and exposure to ultraviolet light.

Common biofilm-forming bacteria include *Pseudomonas aeruginosa* and *Staphylococcus epidermidis*, both of which are commonly present in water, air, soil, and skin. According to the Center for Biofilm Engineering at Montana State University, biofilm forms when bacteria adhere to surfaces in moist environments by excreting a slimy, glue-like substance. This slimy excretion is referred to as the extracellular polymeric substance (EPS) which holds the bacteria in the biofilm matrix. The bacteria form a biofilm in three phases: attachment, growth, and dispersal.

A biofilm is a serious form of a bacterial infection because surface attachment and colonization provides additional protection against environmental changes, including antibiotic medications. The antibiotics in use today were created using studies of bacteria suspended in agar, or free-floating bacteria. However, it has been discovered in recent years that several bacteria preferentially attach to various substrates, both living and inert, and are highly adaptable organisms that exhibit survival skills in this form. Further, microbial biofilms are tolerant of antibiotic doses up to 1,000 times greater than those of planktonic bacteria (CBE).

Wound infections are not only expensive complications following surgery but still after many years are a major source of bacteria that drive the nosocomial infection rates in hospitals. These infections can complicate illness, cause anxiety, increase patient discomfort and can lead to death. In the biofilm form, bacteria can become recalcitrant to antimicrobials and host defenses, posing a rapidly escalating threat to human health. Typical antimicrobial and antibiotic treatments for these biofilm based infections run the risk of developing antimicrobial and antibiotic resistant strains of bacteria. There remains a need for biophysical treatments not subject to bacteria resistance.

SUMMARY

Disclosed and described herein are antimicrobial dressings for a wound. One of the dressings comprise a substrate; at least one pair of electrodes positioned on or within the substrate, wherein the pair of electrodes comprise a conductive anode in contact with at least a first portion of the wound and a conductive cathode in contact with at least a second portion of the wound; and an energy source connected to at least one electrode pair, wherein the energy source induces an electrical current to flow from the conductive anode, through the wound, to the conductive cathode.

Optionally or alternatively, the electrode pair can be positioned on a singular substrate, or the substrate may comprise a plurality of substrates and the conductive anode can be positioned on a first substrate while the conductive cathode is positioned on a second substrate. Generally, the substrate is comprised of material that is substantially electrically insulating such as, for example, silk or polyester. In one dress, the substrate is comprised of silk and the silk comprises Habotai silk.

Generally, moisture of the wound reduces electrical resistance and facilitates flow of the electrical current through the wound. The moisture may be natural moisture inherent to a wound, or one dressing may include means for adding moisture to the wound. For example, one dressing may include a reservoir that is attached to or is separate from the substrate that contains a fluid such as a sterile saline solution for moistening the wound.

Alternatively or optionally, at least one of the conductive anode and the conductive cathode can be comprised of silver, silver chloride, silver compounds, gold, gold compounds, platinum, platinum compounds, or any other biocompatible electrically-conductive material.

In some dressings, the conductive anode is larger than the conductive cathode. For example, the conductive anode may substantially covers the wound. The size and shape of the dressings and/or the conductive anode or conductive cathode can be conformed to the wound. For example, the conductive anode can be conformed to a shape such that it substantially covers the wound. The size and shape of the antimicrobial dressing can be determined by at least one of wound size, wound shape, and location of the wound. Similarly, in some dressings, the size and shape of at least one of the conductive anode and the conductive cathode can be determined by at least one of wound size, wound shape, and location of the wound. In one non-limiting example, the pair of electrodes positioned on or within the substrate comprise a comb pattern, wherein the anode is larger than the cathode.

In some dressings, at least one of the conductive anode and the conductive cathode are printed on the substrate. For example, the conductive anode and/or the conductive cathode can be printed on the substrate using screen-printing techniques or are printed on the substrate using a printer. In other dressings, at least one of the conductive anode and the conductive cathode are woven into the substrate. For example, at least one of the conductive anode and the conductive cathode can comprise a conductive silver material woven into a Habotai silk substrate.

Alternatively or optionally, the energy source connected to the at least one electrode pair comprises a battery. The battery may be attached to the antimicrobial dressing. For example, the battery may be attached to the substrate. In other dressings the battery is separate from the antimicrobial dressing.

In other dressings, the energy source connected to the at least one electrode pair comprises a plurality of electrodes in a spaced pattern on the substrate that are in contact with the wound and a first subset of the plurality of electrodes are connected in electrical series with the anode and a second set of the plurality of electrodes are connected in electrical series with the cathode. The electrodes are comprised of a biocompatible reduction/oxidation reaction material such that a voltage differential is created between the anode and the cathode. The voltage differential causes the electrical current to flow from the conductive anode, through the wound, to the conductive cathode. For example, the biocompatible reduction/oxidation reaction materials of the electrodes may comprise silver and zinc such that the first subset of the plurality of electrodes are comprised of silver and the second subset of the plurality of electrodes are comprised of zinc. Generally, each electrode power creates a voltage potential of approximately 0.2 volts. In one non-limiting example, enough electrodes are connected in series to the anode and the cathode such that the voltage differential created between the anode and the cathode is approximately 6 volts.

In other dressings, the energy source connected to the at least one electrode pair comprises an energy harvesting device. For example, the energy harvesting device creates a voltage differential between the anode and the cathode, wherein the voltage differential causes the electrical current to flow from the conductive anode, through the wound, to the conductive cathode, based on movement of a subject to whom the antimicrobial dressing is applied.

In other dressings, the energy source connected to the at least one electrode pair may comprise an alternating-current (AC) energy source. The AC energy source may be attached to the antimicrobial dressing. For example, the AC energy source may be attached to the substrate. In other dressings, the AC energy source may be separate from the antimicrobial dressing.

Alternatively or optionally, dressings may include a barrier that substantially covers a side of the substrate opposite the wound. The barrier is generally configured to maintain a desired moisture level of the wound. For example, the barrier may be waterproof or water-resistant.

Alternatively or optionally, dressings may further comprise a current-limiting element. The current limiting element limits the electrical current flowing from the conductive anode, through the wound, to the conductive cathode to a desired range. For example, the desired range of the current flowing through the wound may be 15 milliamps, or less. In some dressings, the desired range of the current flowing through the wound is 10 milliamps, or less. Generally, the current limiting element limits the current such that an unacceptable level of heating caused by the electrical current flowing from the conductive anode, through the wound, to the conductive cathode is not experienced. For example, the current-limiting element may limit current such that a power density applied to the wound is at or below approximately 0.25 W/cm$^2$ to avoid the unacceptable levels of heating caused by the electrical current flowing from the conductive anode, through the wound, to the conductive cathode.

Alternatively or optionally, dressings may include a voltage indicator, wherein the voltage indicator indicates voltage being provided by the energy source connected to the at least one electrode pair and/or a current indicator, wherein the current indicator indicates the presence of electrical current flowing from the conductive anode, through the wound, to the conductive cathode.

Alternatively or optionally, dressings may include a plurality of electrodes in a spaced pattern on the substrate that are electrically isolated from one another on the substrate and are in contact with the wound. The plurality of electrodes are comprised of a biocompatible reduction/oxidation reaction material such that an electrical field is created in the wound by the plurality of electrodes that facilitates wound healing.

In the dressings described herein, the electrical current flowing from the conductive anode, through the wound, to the conductive cathode inhibits biofilm formation within the wound. Further, the electrical current flowing from the conductive anode, through the wound, to the conductive cathode can at least partially disrupt a biofilm growing within the wound. Also, the electrical current flowing from the conductive anode, through the wound, to the conductive cathode at least partially destroys sessile bacteria and/or planktonic bacteria within the wound.

As used herein, the term "wound" includes any exudate of the wound.

Further disclosed and described herein are methods of treating a bacterial infection in a wound (e.g., inhibiting or disrupting bacterial growth or inhibiting or disrupting biofilm in a wound) with the antimicrobial dressings described herein. One such method comprises applying an antimicrobial dressing to the wound; and applying a therapeutically effective amount of an electric current to the wound from the antimicrobial dressing.

Further disclosed herein are methods of assembling or manufacturing the antimicrobial dressings described herein. The methods may include applying a layer of conductive material to an insulated base substrate to form at least one electrode pair on the insulated base substrate, wherein the pair of electrodes comprise a conductive anode and a conductive cathode that are electrically insulated from one another; and connecting an energy source to the at least one electrode pair, wherein the energy source induces an electrical current to flow from the conductive anode, through a wound, to the conductive cathode. In some dressings, the substrate is comprised of silk or polyester. For example, the substrate may be comprised of silk and the silk may comprise Habotai silk. In some dressings, at least one of the conductive anode and the conductive cathode are comprised of silver, silver chloride, silver compounds, gold, gold compounds, platinum, platinum compounds, or any other biocompatible electrically-conductive material.

Generally, dressings are assembled such that the conductive anode is larger than the conductive cathode. For example, the conductive anode may be configured to substantially cover the wound or conform to the shape of the wound.

The antimicrobial dressings may be assembled such that the size and shape of the antimicrobial dressing is determined by at least one of wound size, wound shape, and location of the wound. Similarly, the dressings may be assembled such that the size and shape of at least one of the conductive anode and the conductive cathode is determined by at least one of wound size, wound shape, and location of the wound.

Assembling the dressing may include printing at least one of the conductive anode and the conductive cathode on the substrate. Printing may include screen-printing techniques, printing on the substrate using a printer, or any other method of printing the conductive anode and/or cathode on the substrate.

In some dressings, the assembly includes weaving at least one of the conductive anode and the conductive cathode are woven into the substrate. For example, at least one of the conductive anode and the conductive cathode comprise a conductive silver material woven into a Habotai silk substrate.

In some dressings, assembly may include supplying a battery as the energy source connected to the at least one electrode pair.

In some dressings, assembly may include forming a plurality of electrodes in a spaced pattern on the substrate, wherein the energy source connected to the at least one electrode pair comprises the plurality of electrodes in a spaced pattern on the substrate that are in contact with the wound and a first subset of the plurality of electrodes are connected in electrical series with the anode and a second set of the plurality of electrodes are connected in electrical series with the cathode and the plurality of electrodes are comprised of a biocompatible reduction/oxidation reaction material such that a voltage differential is created between the anode and the cathode, wherein said voltage differential causes the electrical current to flow from the conductive anode, through the wound, to the conductive cathode. For example, the biocompatible reduction/oxidation reaction materials may comprise silver and zinc such that the first subset of the plurality of electrodes are comprised of silver and the second subset of the plurality of electrodes are comprised of zinc.

In some dressings, assembly may include forming a barrier that substantially covers a side of the substrate opposite the wound, said barrier configured to maintain a desired moisture level of the wound.

In some dressings, assembly may include any one or more of providing a current-limiting element, wherein the current limiting element limits the electrical current flowing from the conductive anode, through the wound, to the conductive cathode to a desired range, providing a voltage indicator, wherein the voltage indicator indicates voltage being provided by the energy source connected to the at least one electrode pair, and/or providing a current indicator, wherein the current indicator indicates the presence of the electrical current flowing from the conductive anode, through the wound, to the conductive cathode.

In some dressings, assembly may include forming a plurality of unconnected electrodes in a spaced pattern on the substrate that are electrically isolated from one another on the substrate, the plurality of unconnected electrodes comprised of a biocompatible reduction/oxidation reaction material such that an electrical field is created in the wound by the plurality of unconnected electrodes thus facilitating wound healing.

Additional advantages will be set forth in part in the description which follows or may be learned by practice.

The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

The disclosure will be readily understood by the following detailed description in conjunction with the accompanying drawings, wherein like reference numerals designate like structural elements, and in which:

FIG. 1 is a simplified electrical schematic of an antimicrobial dressing for a wound;

FIG. 2A is a cross-section/profile view of an antimicrobial dressing;

FIG. 2B is a plan view showing the wound side of an antimicrobial dressing;

FIG. 2C is an illustration of an antimicrobial dressing showing an on-board reservoir with appropriate tubing that is used to apply moisture to the wound while the antimicrobial dressing is in place;

FIG. 2G is an illustration of an antimicrobial dressing that optionally includes a barrier that covers a part of or substantially covers a side of the substrate opposite the wound;

FIG. 2H illustrates an example of an antimicrobial dressing that further comprise a current-limiting element;

FIG. 2I illustrates electrical impedance spectroscopy (EIS) measurements on exemplary pig burn wounds that can be used to determine healing in the wound;

FIG. 2J illustrates non-contact eddy current measurements were also performed on exemplary pig burn wounds, which can also be used to determine wound healing;

FIG. 2K is an illustration that shows biofilm formed in the wound;

FIG. 5C shows an exemplary final bandage design for testing and examples of printed dressings;

FIG. 6 is a photograph of a current measurement setup with 6V battery pack, large positive electrode dressing (30 mm spacing) embedded in agar and Keithley 2100 Digital Multimeter;

DETAILED DESCRIPTION

Figure 2E:
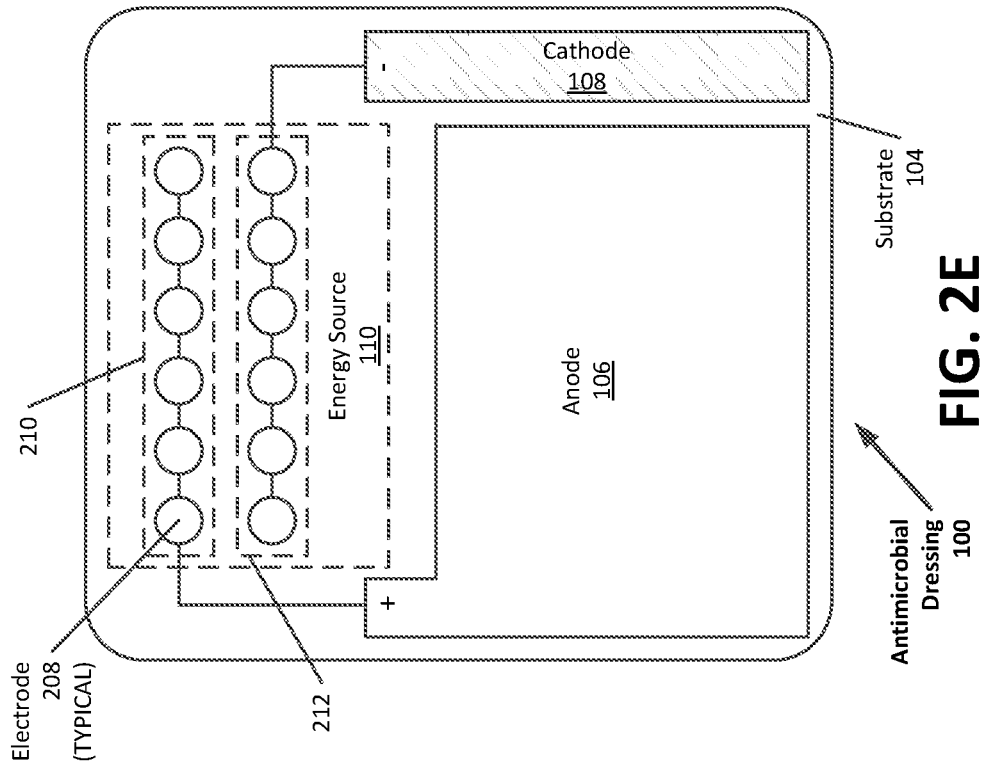
FIG. 2E illustrates another embodiment of an antimicrobial dressing having an alternate form of an energy source.
Figure 2D:
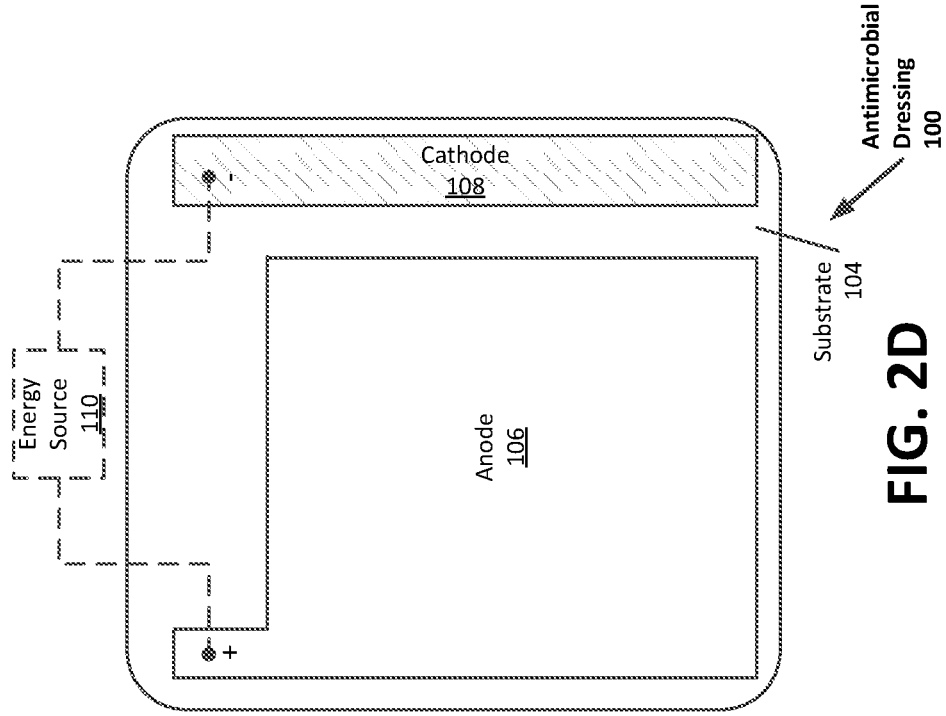
FIG. 2D is an illustration of an antimicrobial dressing with all or a portion of the energy source separate from the substrate.

In the United States, 6.5 million patients are affected by chronic wounds, sometimes complicated by infection. If the bacteria form a biofilm at the wound site, treatment of the infection becomes significantly more difficult. Biofilm bacteria are 500 to 5,000 times more resistant to antibiotic medications than the non-biofilm bacteria. Previous studies have shown that the presence of direct electric current through the biofilm enhances the activity of various antibiotics against biofilm-forming bacterial strains such as *Pseudomonas aeruginosa* and *Staphylococcus epidermidis*. This behavior has been referred to as the electro-bactericidal effect.

Disclosed herein are antimicrobial wound care dressings and methods of using the antimicrobial wound care dressings for wound treatment in humans and animals. The antimicrobial wound care dressings can be used to apply an electric current through a wound to aid in bacterial infection prevention and destruction. These dressings can provide a functional antimicrobial and antibiofilm barrier.

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes—from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

In one aspect, disclosed are wound care dressings that include an electrode assembly and an electric current generating and control assembly. The electrode assembly can be used for applying an electric current for wound healing. The electric current generating and control assembly can be used to control and vary the electric current intensity during the wound healing period. The wound care dressings can provide antimicrobial and antibiofilm effects, which aid wound healing and tissue regeneration.

FIG. 1 is a simplified electrical schematic of an antimicrobial dressing 100 for a wound. In this schematic, the wound 102 is represented as an electrical resistor. The dressing 100 comprises a substrate 104 and at least one pair of electrodes positioned on or within the substrate 104. The pair of electrodes comprise a conductive anode 106 in contact with at least a first portion of the wound 102 and a conductive cathode 108 in contact with at least a second portion of the wound 102. Further comprising the schematic of an antimicrobial dressing 100 is an energy source 110. The energy source 110 is connected to the electrode pair 106,

108. The anode 106 and the cathode 108 are electrically insulated from one another. The energy source 110 induces a voltage differential between conductive anode 106 and conductive cathode 108, which causes an electrical current (I) to flow from the conductive anode 106, through the wound 102 (represented here as an electrical resistor), to the conductive cathode 108.

FIGS. 2A and 2B are physical representations of the schematic of an antimicrobial dressing 100 for a wound. FIG. 2A is a cross-section/profile view of the antimicrobial dressing 100 and FIG. 2B is a plan view showing the wound side of the antimicrobial dressing 100. In FIG. 2B the energy source 110 and wiring is shown in dashed lines to represent that it is located on the substrate 104 on the side opposite the wound side. It is also to be appreciated that the energy source 110 may be located off of or remote from the substrate 104. Further, though FIGS. 2A and 2B illustrate only a single electrode pair—anode 106 and cathode 108, it is to be appreciated that the antimicrobial dressing 100 may be comprised of any number of electrode pairs 106, 108 in electrical communication with energy source 110 or even a plurality of energy sources 110 that are equal to or less than the number of electrode pairs. In non-limiting examples, the electrodes 106, 108 may have a thickness of 25 μm to 500 μm, 50 μm to 400 μm, 75 μm to 300 μm, or 100 μm to 200 μm and the anode 106 may have a thickness that differs from the cathode 108.

Also, though FIGS. 2A and 2B depict a singular, monolithic substrate 104, it is to be appreciated that the substrate 104 may be comprised of one, two or even more separate portions. For example, the electrode pair 106, 108 may be positioned on a singular substrate 104, or the substrate 104 may comprise a plurality of substrates and the conductive anode 106 may be positioned on a first substrate and the conductive cathode 108 may be positioned on a second substrate.

Generally, in regard to the substrate 104, it is comprised of material that is substantially electrically insulating. For example, the substrate 104 may be comprised of silk, polyester, and any material that has ability for printing a desired geometry and is compatible with a wound environment (i.e., does not occlude the wound for transport of essential fluids including oxygen) including polymeric substrates common to the medical industry like Polydimethylsiloxane (PDMS) and the like. In one embodiment of the dressings 100, the substrate 104 is comprised of silk and the silk comprises Habotai silk. In other embodiments the substrate 104 may be comprised of semiconductive materials or may have conductive elements within the substrate. For example, at least one of the conductive anode 106 or the conductive cathode 108 may be woven into the substrate 104. In one specific example, at least one of the conductive anode 106 or the conductive cathode 108 comprise a conductive silver material woven into a Habotai silk substrate 104. In one non-limiting example, an electrical current may be circulated through the conductive or semiconductive element of the substrate 104 in parallel to the current that flows from the conductive anode 106, through the wound 102, to the conductive cathode 108. The current through the substrate may create an electrical field that can facilitate healing of the wound. Generally, the substrate 104 or at least the wound side portion of the substrate 104 is sterile. Non-limiting examples of substrate 104 thickness include 10 μm-1 mm or 10 μm-0.5 mm.

In other examples, at least one of the conductive anode 106 or the conductive cathode 108 may be printed on the substrate using conductive printing techniques. For example, at least one of the conductive anode 106 or the conductive cathode 108 may be printed on the substrate using screen-printing techniques, using a (conductive) ink-jet printer, and the like. It is to be appreciated that any other deposition or incorporation methods may be used to form the conductive anode 106 and conductive cathode 108 on or within the substrate 104.

Generally, the conductive anode 106 and the conductive cathode are comprised of biocompatible electrically-conductive materials. Examples of such materials include silver, silver chloride, silver compounds, gold, gold compounds, platinum, platinum compounds, and/or binary alloys of platinum, nickel, cobalt or palladium with phosphorus, or binary alloys of platinum, nickel, cobalt or palladium with boron, and the like. Non-metallic materials are also contemplated for electrode formation such as conductive polymers and the like. Conductive polymers can include, but are not limited to, polyaniline, polythiophene, polypyrrole, polyphenylene, poly(phenylenevinylene), and the like.

The conductive anode 106 and the conductive cathode 108 may be of any size and/or shape. Generally; however, as shown in FIG. 2B the conductive anode 106 is larger than the conductive cathode 108. In one example, the conductive anode 106 substantially covers the wound. For example, the conductive anode 106 can be conformed to a shape such that it substantially covers the wound. Similarly, the size and shape of at least one of the conductive anode 106 and the conductive cathode 108 can be determined by at least one of wound size, wound shape, and location of the wound. Likewise, the size and shape of the antimicrobial dressing 100 can be determined by at least one of wound size, wound shape, and location of the wound. The antimicrobial dressings can be formed into any of a number of possible shapes, patterns or geometries, depending upon the application and topography of the wound or application site. Any aspect of the wound dressing can be manufactured in a variety of shapes and configurations. For example, configurations can include, but are not limited to, compressive wraps, tampons, tubular, roll gauze, pads of varying sizes and shapes, island dressings, strip dressings, dressings for dental applications, rectal dressings, vaginal pads, surgical packing or dressings, or any combination thereof. Spacing between the conductive anode 106 and the conductive cathode 108 may also depend upon wound size, location and shape. Generally, it is desired to have the conductive anode 106 and conductive cathode 108 as close together as possible without causing an electrical short-circuit. Exemplary feature spacings include, without limitation, from about 10 nm to about 10 mm, from about 10 nm to about 200 μm, from about 100 nm to about 100 μm, from about 1 μm to about 100 μm, or from about 1 μm to about 100 μm. FIGS. 3A-3G are non-limiting examples of various size, spacing and shapes of the conductive anodes 106 (shown with the "+" signs in FIGS. 3A-3G) and conductive cathodes (shown with the "−" signs in FIGS. 3A-3G) although the electrodes can take any of a variety of appropriate configurations. The disclosed antimicrobial dressings can include a configuration of electrodes 106, 108 that can generate both shallow (e.g., 1 μm-2 mm, or 1 μm-1 mm), and deep (e.g., 1 mm-100 mm, or 2 mm-100 mm) currents into a wound, or a combination thereof.

Referring to FIGS. 2A and 2B, the energy source 110 causes a potential difference between the anode 106 and the cathode 108. In various embodiments, the energy source 110 may be switched or otherwise controlled where control includes at least its on/off state, its voltage, and/or the current that is allowed to flow from the conductive anode 106, through the wound 102, to the conductive cathode 108.

As shown in FIG. 2A, at least a portion of the anode 106 is in contact with at least a portion of the wound 102 or exudate 202 of the wound. Similarly, at least a portion of the cathode 108 is in contact with at least a portion of the wound 102 or exudate 202 of the wound. It is desirable for the wound 102 or the exudate 202 to be moist. Moisture of the wound 102 or the exudate 202 reduces electrical resistance and facilitates flow of the electrical current through the wound 102. The moisture may be from the natural secretions and exudate that is inherent to a wound, or it may be from moisture that is added to the wound. For example, the wound 102 may be moistened with sterile saline, water, gels, antibiotic creams and lotions, and the like. Such moistening agents may be applied directly to the wound 102 before placement of the antimicrobial dressing 100. In other aspects, the antimicrobial dressing 100 may include means for moistening the wound 102. For example, as shown in FIG. 2C, a reservoir 204 with appropriate tubing 206 may be used to apply moisture to the wound 102 while the antimicrobial dressing 100 is in place. The tubing may be configured such that the rate of moisture flowing from the reservoir 204 to the wound 102 can be controlled to avoid saturating the substrate 104. Though shown located on the substrate 104, it is to be appreciated that the reservoir 204 may be located separate from the substrate 104. Any other means may also be used for moistening the wound 102.

As shown in FIGS. 1, and 2A-2D, the antimicrobial dressing 100 includes an energy source 110. The energy source 110 may be attached to the substrate 104 (see FIG. 2B), or all or a portion of the energy source may be separate from the substrate 104 (see FIG. 2D). The energy source 110 can comprise any device or any means for creating a potential difference between the conductive anode 106 and the conductive cathode 108. Generally, the potential difference is at approximately 6 volts, though voltages of other values may also be used. The energy source 110 may be an alternating-current (AC) or a direct current (DC) source, or combinations thereof. The energy source 110 may be an AC source rectified to become DC, or a DC source inverted to become AC. Frequency dependent energy source 110 can have any of a variety of appropriate wave forms including, but not limited to, square, sinusoidal, triangular, trapezoidal, or more complex patterns. AC sources can be modulated in any of a variety of ways including temporally and spatially.

In one aspect, the energy source 110 comprises a battery, which may include any number of cells connected in either series and/or parallel. In one aspect, the energy source 110 may comprise a battery paired with an inverter to create an AC source or it may be an AC source transformed to the desired voltage. In one exemplary embodiment, the energy source 110 connected to the at least one electrode pair comprises an energy harvesting device that creates the voltage differential between the anode 106 and the cathode 108. For example, the energy harvesting device may be of the type that creates the voltage differential between the anode 106 and the cathode 108 based on movement of a subject to whom the antimicrobial dressing is applied. Further, the energy source 110 may at least in part use a galvanic reaction between the anode 106, the wound 102, and the cathode 108 to create a voltage differential between the anode 106 and the cathode 108, which results in the electrical current flowing from the conductive anode 106, through the wound 102, to the conductive cathode 108.

FIG. 2E illustrates another embodiment of an antimicrobial dressing 100 having an alternate form of an energy source 110. In this example, the energy source 110 connected to the at least one electrode pair 106, 108 comprises a plurality of electrodes 208 in a spaced pattern on the substrate that are substantially in contact with the wound 102 and/or the exudate 202. A first subset 210 of the plurality of electrodes 208 are connected in electrical series and/or electrically parallel with the anode 106 and a second subset 212 of the plurality of electrodes 208 are connected in electrical series and/or electrically parallel with the cathode 108. Generally, the plurality of electrodes 208 are comprised of a biocompatible reduction/oxidation reaction material such that a voltage differential is created between the anode 106 and the cathode 108, wherein the voltage differential causes the electrical current to flow from the conductive anode 106, through the wound 102, to the conductive cathode 108. The number, spacing and materials used in the electrodes 208 can vary and at least these parameters can be used to determine the voltage differential between the anode 106 and the cathode 108. For example, the biocompatible reduction/oxidation reaction materials that comprise the electrodes 208 may be silver and zinc such that the first subset 208 of the plurality of electrodes 210 are comprised of silver and the second subset 212 of the plurality of electrodes 208 are comprised of zinc, or vice-versa. Other biocompatible reduction/oxidation reaction materials may be used to form the electrodes 208. Generally, the voltage potential created between each spaced electrode 208 pair is about 0.2 volts, but as noted herein this can vary depending upon several parameters including, spacing, materials, contact with the wound 102, moisture of the wound 102, and the like.

Figure 2F:
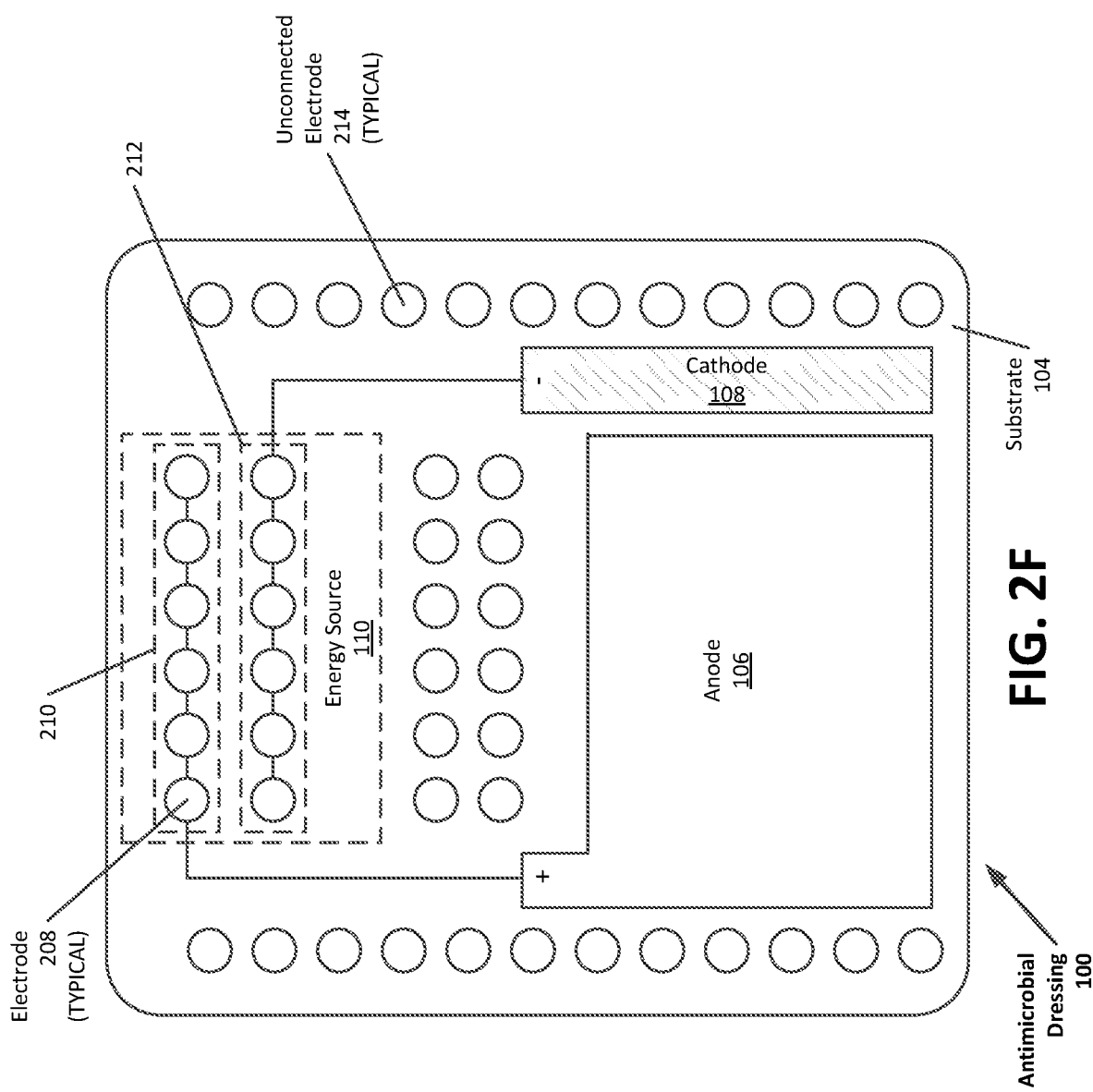
FIG. 2F illustrates an embodiment of an antimicrobial dressing such as the one shown in FIG. 2E, that further comprises a plurality of unconnected electrodes in a spaced pattern on the substrate that are electrically isolated from one another on the substrate.
Figure 3A:
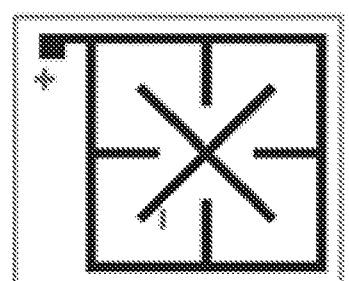
FIGS. 3A-3G are non-limiting examples of various size, spacing and shapes of conductive anodes.
Figure 3B:
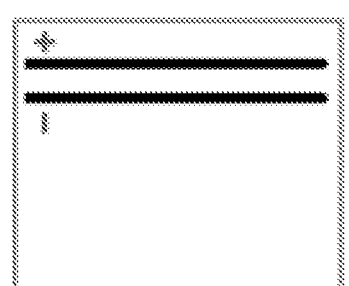
Figure 3C:
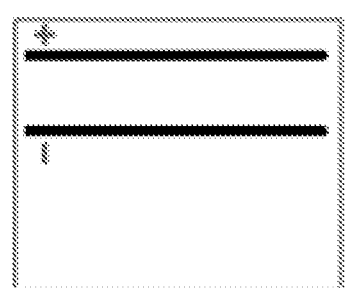
Figure 3D:
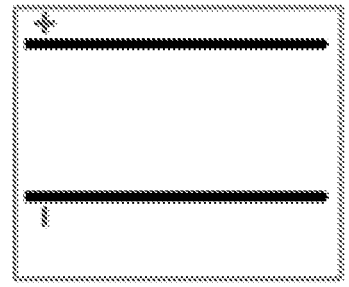
Figure 3E:
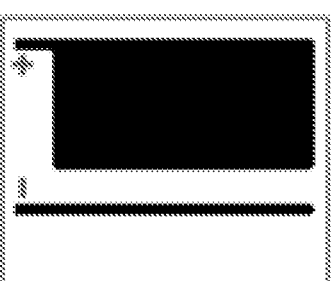
Figure 3F:
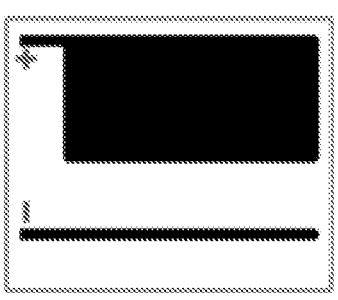
Figure 3G:
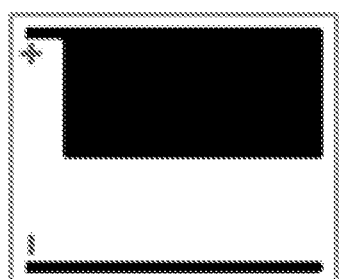

FIG. 2F illustrates an embodiment of an antimicrobial dressing such as the one shown in FIG. 2E, that further comprises a plurality of unconnected electrodes 214 in a spaced pattern on the substrate 104 that are electrically isolated from one another on the substrate 104 and are substantially in contact with the wound 102 and/or the exudate 202. The plurality of unconnected electrodes 214 are comprised of a biocompatible reduction/oxidation reaction material such that an electrical field is created in and around the wound 102 by the plurality of unconnected electrodes 214, thus facilitating wound healing. It is to be appreciated that although FIG. 2F shows the energy source 110 comprising a plurality of electrodes 208 in a spaced pattern on the substrate 104, the plurality of unconnected electrodes 214 in a spaced pattern on the substrate 104 that are electrically isolated from one another on the substrate 104 are not limited to this embodiment. The unconnected electrodes 214 can be used with any energy source 110 that create a potential difference between the anode 106 and the cathode 108 including a battery, an AC source, a DC source, an energy harvesting device, and the like.

In one aspect, as shown in FIG. 2G, the antimicrobial dressing 100 can optionally include a barrier 216 that covers a part of or substantially covers a side of the substrate 104 opposite the wound 104. Among other things, the barrier 216 is configured to maintain a desired moisture level of the wound 102 and/or prevent contamination of the substrate 104 and the antimicrobial dressing 100. Generally, the barrier 216 is waterproof or water-resistant such that moisture is retained within the wound 102 and outside moisture is prevented from entering the wound 102. The barrier 216 can be any biocompatible semi-permeable or impermeable material for limiting the evaporation of moisture from the substrate 104 and/or the wound surface. The barrier 216 can be fixedly attached to the substrate 104 and/or the skin of the subject or removably attached for easy removal and replacement.

The barrier 216 can control the rate of moisture evaporation from the substrate and/or the wound 102, and also function as a physical barrier to the penetration of microbes from the surrounding environment. The barrier 216 can be a film, fabric or foam. Some preferred materials include, but are not limited to, polyurethanes, polyolefins such as linear low density polyethylene, low density polyethylene, ethylene vinyl acetate, vinylidene, chloride copolymer of vinyl chloride, methyl acrylate or methyl methacrylate copolymers and combinations thereof. A preferred polymeric material is polyurethane, either as a film or as a polyurethane foam. The polyurethane may be an ester or ether based polyurethane. Materials suitable for a foam moisture regulation layer can be any semi-permeable or impermeable natural or synthetic compound including, but not limited to, rubber, silicon, polyurethane, polyethylene polyvinyl, polyolefin, hydrogels, or combinations thereof.

Alternatively, the barrier 216 may be a transparent elastomer film for visual inspection of the moisture status of the substrate 104. The film can have a thickness from 10 µm to 100 µm. The barrier 216 may have an MVTR of from about 300 to about 5,000 grams/meter2/24 hours, preferably from about 800 to about 2,000 grams/meter2/24 hours. The barrier 216 can be laminated to the substrate 104 by methods well recognized in the art.

The antimicrobial dressing 100 can optionally include one or more therapeutic agents. Exemplary therapeutic agents include, but are not limited to, growth factors, analgesics (e.g., an NSAID, a COX-2 inhibitor, an opioid, a glucocorticoid agent, a steroid, or a mineralocorticoid agent), antibiotics, antifungals, anti-inflammatory agents, antimicrobials (e.g., chlorhexidine-, iodine-, or silver-based agents), antiseptics (e.g., an alcohol, a quaternary ammonium compound), antiproliferative agents, emollients, hemostatic agents, procoagulative agents, anticoagulative agents, immune modulators, proteins, vitamins, and the like.

FIG. 2H illustrates an example of an antimicrobial dressing 100 that further comprise a current-limiting element 220, as known in the art. In one aspect, the current-limiting element may be integrated with an into the energy source 110. In other aspects, it is a stand-alone element. The current-limiting element 220 may be, for example, an inductor, resistors or a resistor bridge, a current-limiting circuit, and the like. The purpose of the current limiting element is to limit the electrical current flowing from the conductive anode 106, through the wound 102, to the conductive cathode 108 to a desired range or to less than a maximum value. For example, the desired range of the current flowing through the wound 102 may 15 milliamps, or less. In other aspects, the desired range of the current flowing through the wound 102 may be 10 milliamps, or less. Generally, current is limited so that an unacceptable level of heating caused by the electrical current flowing from the conductive anode 106, through the wound 102, to the conductive cathode 108 is not experienced. For example, it may be desire that power density applied to the wound is at or below governmentally-regulated standards to prevent unacceptable heating in the wound. In the United States, such regulations may be promulgated by the Food and Drug Administration (FDA). For example, power density may be required to be at or below approximately 0.25 W/cm$^2$ to avoid unacceptable levels of heating. Though not shown in FIG. 2H, other embodiments of the antimicrobial dressing 100 may include, for example, a voltage indicator that indicates voltage is being provided by the energy source 110 connected to the at least one electrode pair 106, 108 and/or a current indicator that indicates the presence of electrical current flowing from the conductive anode 106, through the wound 102, to the conductive cathode 108. Optionally, other embodiments of the antimicrobial dressing 100 may include a sensor. In one aspect, the sensor may comprise an electrical impedance spectroscopy (EIS) probe that senses impedance through the wound 102. In another aspect, the sensor may comprise an eddy current probe. The measured impedance through the wound 102 can be used to detect wound healing. For example, as shown in FIG. 2I, EIS measurements on exemplary pig burn wounds were shown to increase and level off as the wound healed. Non-contact eddy current measurements were also performed on exemplary pig burn wounds. Eddy current measurement is performed by first recording voltage in air away from wound (null measurement) for 5 seconds. The eddy current probe is then brought into contact with the wound and the voltage is recorded for another 5 seconds. The results of these measurements are shown in FIG. 2J. A single measurement is recorded as |ΔVDC| which is the absolute difference between the average of the two measurements. Each bar is an average of 5 measurements on 6 different wound sites (Total 30 measurements). Data are mean±SD; $p<0.01$ vs pre-burn; $p<0.05$ vs day 0.

FIG. 2K is an illustration that shows biofilm 222, as described herein, formed in the wound 102. Biofilm 222 can be resistant to antibiotics and other forms of medicinal treatment. As shown in FIG. 2J, the electrical current flowing from the conductive anode 106, through the wound 102, to the conductive cathode 108 can inhibit biofilm 222 formation within the wound 102. Furthermore, the electrical current flowing from the conductive anode 106, through the wound 102, to the conductive cathode 108 can at least partially disrupt a biofilm 222 growing within the wound. Even bacteria that has not formed a biofilm can be disrupted and/or destroyed by the antimicrobial dressing. The electrical current flowing from the conductive anode 106, through the wound 102, to the conductive cathode 108 can at least partially destroys sessile and/or planktonic bacteria within the wound 102.

The antimicrobial dressings disclosed herein can be fabricated by various methods. The electrodes can be fabricated from the conductive materials disclosed herein.

In an exemplary embodiment, the antimicrobial dressing fabrication process can begin with applying the at least one pair of conductive electrodes 106, 108 to the substrate 104. This step may involve printing techniques such as screen-printing or using an ink-jet printer, among other methods.

Also, in certain embodiments, electrodes 106, 108 can be fabricated by stamping a solution of conductive polymer or precursor(s) thereof onto the substrate 104. Any of a variety of known methods for stamping can be used to fabricate the electrodes. In certain embodiments, electrodes can be fabricated using a capillary micromolding technique and/or apparatus. In certain embodiments, electrodes can be fabricated by printing conductive polymer and/or prepolymer directly onto an appropriate substrate 104. In one example an ordinary laser printer is used in combination with specially formulated ink to form a patterned conductive polymer film. An appropriate ink formulation can comprise a conductive polymer and/or prepolymer thereof. Additionally, such an ink may optionally comprise a binder, a surfactant, and/or an oxidizing agent such as ferric ethylbenzenesulfonate. In one example, a substrate 104 coated with an appropriate ink is exposed to excess monomer vapor thereby developing the image in the regions containing oxidizing agent. This results in a conductive polymer image. In certain embodiments, a laser printer can be used to print a negative image of an electrode. The negative can then be dipped into a conductive polymer deposition/coating system. This results in polymer coating both the negative image and the exposed substrate 104. Then the image can be developed by removing the toner. In one example, a negative image of an interdigitated electrode (IDE) can be printed on an ordinary overhead transparency using a laser printer. The conductive polymer can then be formed in situ. In certain embodiments, electrodes can be fabricated photolithographically.

The layers of disclosed antimicrobial dressings may or may not be attached to each other or can be provided as a component of another structure. For example, an electrode including a patterned conductive layer on a base substrate can be applied directly to the affected site, such as a wound. The energy source can be integral with or supplied separately from the electrode assembly of the antimicrobial dressings.

The disclosed antimicrobial dressings can be used to treat wounds of an animal or human subject. The appropriate aspect of the wound dressing can be selected and positioned on the wound, with the electrodes in direct contact or indirect contact with the wound.

In one aspect, disclosed is a method of treating or preventing a bacterial infection (e.g., a biofilm infection) in a wound, the method including applying a therapeutically effective amount of an electric current to the wound. The electric current can be applied to the wound via a antimicrobial dressing as disclosed herein. The antimicrobial dressing can include an anode and a cathode that are substantially in contact with the wound or its exudate such that an electric current flows through the wound. As a non-limiting example, the voltage potential between the anode and the cathode may be from 1-10 volts. The time of treatment may range from hours to days. The antimicrobial dressing can be applied, for example, within 4-6 hours of injury to prevent biofilm formation. The antimicrobial dressing can be applied, for example, after biofilm formation (e.g., 7 days after injury) to treat a biofilm infection. The method may reduce the bacterial load by >90% over a period of 4 weeks. For example, the starting bacterial load may be $10^5$-$10^8$ colony forming units (cfu)/ml, where $10^5$ is the clinical infection threshold, and the method of treatment using the antimicrobial dressing reduces the bacterial load to below the clinical threshold (e.g. at or below $10^1$-$10^2$ cfu/ml) in the wound.

EXAMPLES

The present invention has multiple aspects, illustrated by the following non-limiting examples.

A design of the antimicrobial dressings was designed with a large anode area (31.50 cm$^2$) and a small cathode area (2.25 cm$^2$). The total dressing area that would be in contact with the skin was a 75 mm by 75 mm area (56.25 cm$^2$). However, further investigation into the effect of variable electrode spacing was needed. Therefore, three designs were tested: (a) 10 mm spacing, (b) 20 mm spacing, and (c) 30 mm spacing. The series of conductive patterns used in testing are shown in FIGS. 3A-3G. Leads were printed with the bandage pattern for more consistent results.

The reason for using an open circuit conductive pattern design was to force current to travel through the liquid medium and bacteria before reaching ground. If a closed circuit pattern were used, the path of least resistance would be along the pattern and not through the medium. Although this was not studied, a continuous pattern was expected to have less effect on the exclusion of bacteria.

Figure 4:
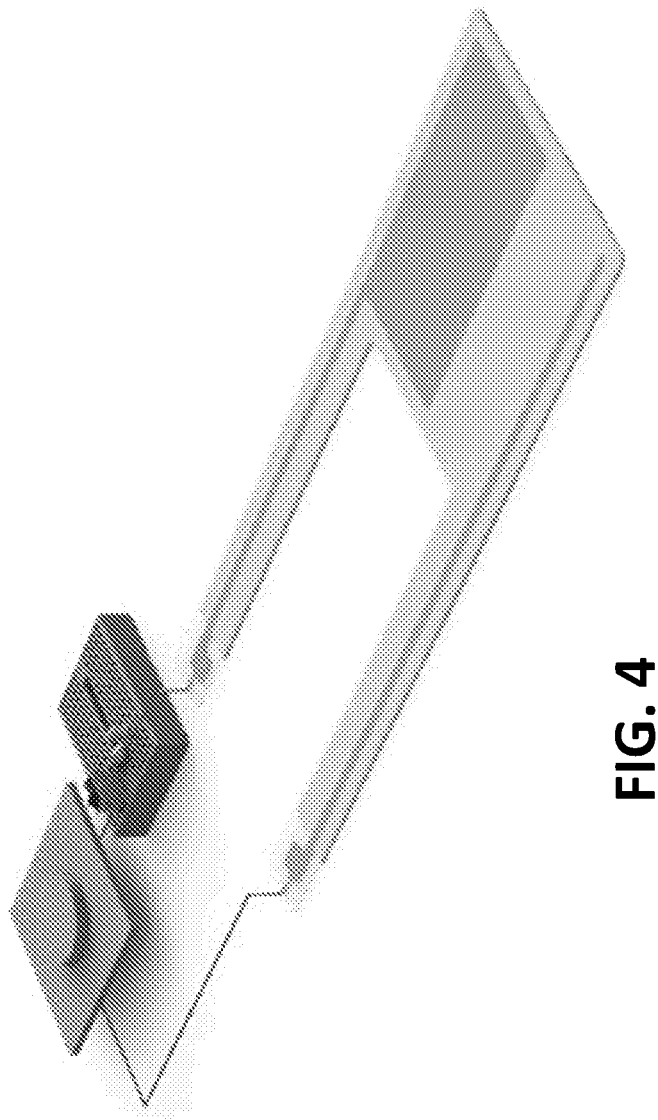
FIG. 4 is a SolidWorks model of an exemplary bandage and battery system.

Another design feature added was an on/off switch for easy user control. Before trials with animals or consented amputee patients, both of which are scheduled to occur in the near future, a small safety circuit should be added between the bandage and the battery to prevent harm from any malfunction that could occur. This circuit would include an on/off switch for easy operation by the user, a resistor to limit the current or a fuse to break the circuit if an unsafe level of current was reached, and an LED to indicate when the switch was on and the bandage was active. A SolidWorks model of the bandage and battery system is shown in FIG. 4, having a large positive electrode bandage connected to battery through a small circuit including an on/off switch, a 500Ω to 6 kΩ resistor, and an LED to indicate with the switch is on and the bandage is active.

Figure 5A:
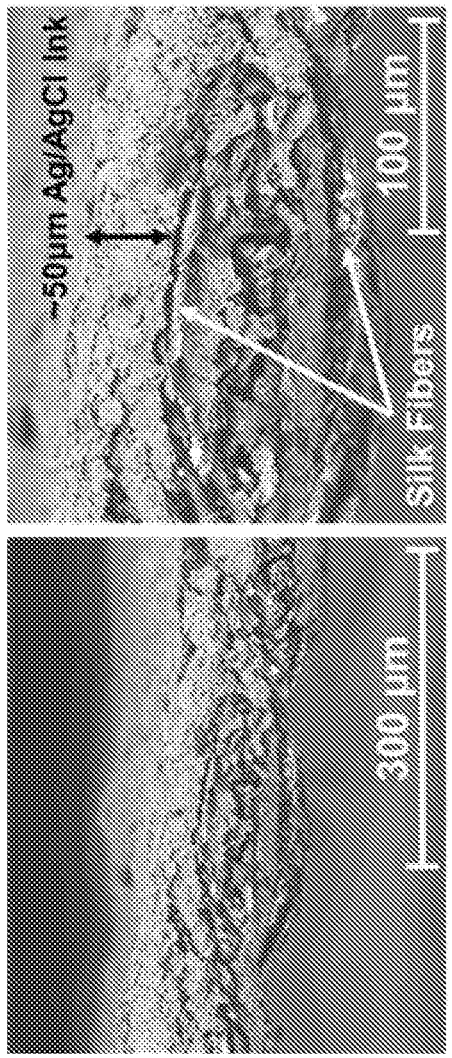
FIG. 5A shows SEM images that were used to characterize the thickness of silver/silver chloride ink deposited on the silk Habotai fabric as well as the extent that penetrates through the full thickness of the fabric.
Figure 5B:
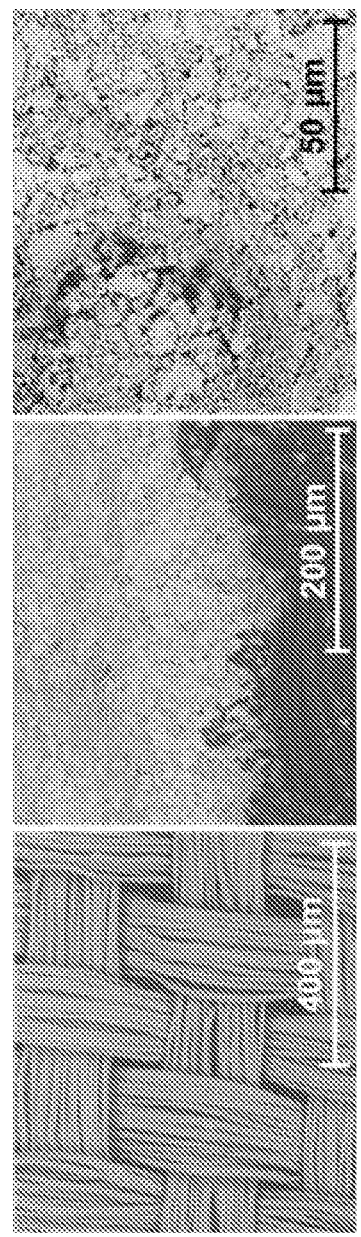
FIG. 5B shows further characterization of the screen-printed silver/silver chloride ink onto silk Habotai fabric that display a top view of the woven Habotai silk (left), the silver/silver chloride ink on silk at a 40° angle from vertical (middle), and a top view of the silver/silver chloride ink.

New bandages were fabricated having a large positive electrode design including silver/silver chloride ink screen printed onto silk Habotai and sealed with a waterproof medical tape backing. Screen printing uniformity was characterized through Scanning Electron Microscopy (SEM) images (FIG. 5A and FIG. 5B). From the images, it was observed that the silver/silver chloride particles, which appears as fluffy gray matter, appeared to penetrate through the full thickness of the silk Habotai fabric, which appears as bands of white fibers. Furthermore, it was observed from the SEM imaging that the silver/silver chloride ink was deposited onto the top of the silk Habotai fabric through screen printing processes in a uniform layer of about 50 µm. FIG. 5B shows further characterization of the screen-printed silver/silver chloride ink onto silk Habotai fabric. These SEMs display a top view of the woven Habotai silk (left), the silver/silver chloride ink on silk at a 40° angle from vertical (middle), and a top view of the silver/silver chloride ink. FIG. 5C shows the final bandage design and examples of printed dressings.

The battery pack comprised a 4-AA battery holder from RadioShack™ with a built in on/off switch and positive and negative lead wires connected inside the housing. This battery pack made operation and connection easier for testing. In order to securely interface the bandage to the new battery pack, stainless steel lead wires (0.012" diameter) were adhered to the lead pads of the printed pattern. Because the Creative Materials 113-09(s) silver/silver chloride ink, used for printing the electrodes, is not solderable, a silver conductive epoxy was used to make a strong and continuous connection to the dressing. The selected epoxy was Ted Pella H20E EPO-TEK Silver Conductive Epoxy. It was rated as low outgassing, non-toxic and compliant with USP Class VI Biocompatibility standards, and therefore a great option to use for these bandages. The epoxy was applied and cured at 150° C. for 5 minutes, per manufacturer instructions. Electrical tape was used to insulate the connection of the bandage lead wires to the battery pack leads.

Brownish pigment observed on the silk substrate around the epoxy was a reaction of the epoxy with the heat from the hot plate during curing. This only occurred when the epoxy was in direct contact with the hot plate through the silk, and did not occur if the epoxy was contained to the bandage lead pad. After the leads were attached, typical resistance measurements from the stainless steel lead wire to the positive electrode were on the order of 1-30Ω depending on the location of the probes.

The in vitro studies performed include current measurements, studies with spotted bacteria, and studies with excised pre-formed biofilm. All in vitro studies presented in the following sections were performed using tryptic soy agar and *Pseudomonas aeruginosa* as the bacteria strain.

Current Measurements

In vitro current measurements were conducted to quantify the amount of current present in the system. This data was important to collect because the FDA requirement for safe contact with skin is a power density below 0.25 W/cm² to prevent thermal burns. Therefore, by collecting direct current data, operation below this thermal burn threshold was confirmed. Two bandages were studied in vitro, embedded in tryptic soy agar and connected to 6V battery packs. The ammeter was connected in series between the negative lead of the bandage and the ground of the battery pack (see FIG. 6), which shows the current measurement setup with 6V battery pack, large positive electrode dressing (30 mm spacing) embedded in agar and Keithley 2100 Digital Multimeter. The direct current results yielded trends as shown in FIG. 7.

Figure 7:
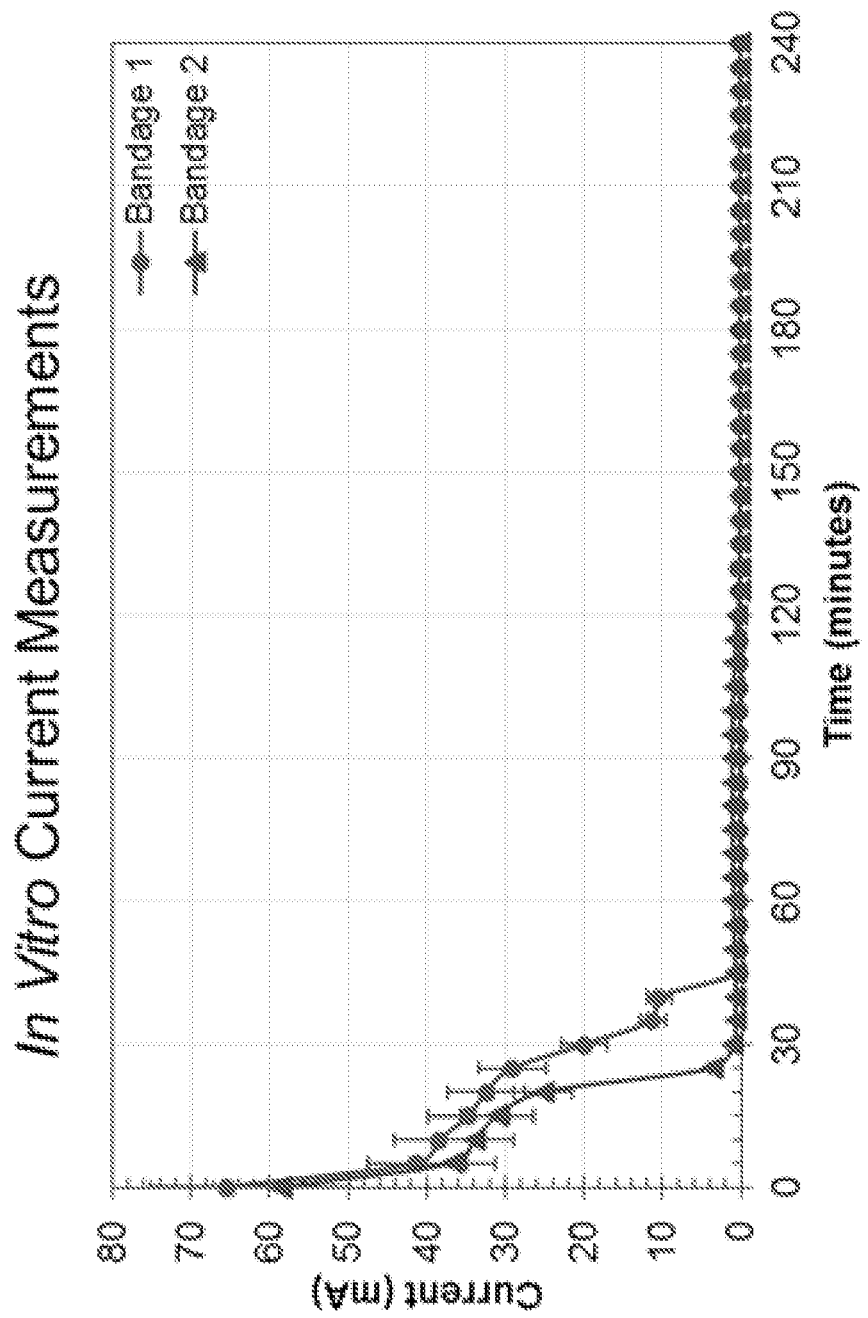
FIG. 7 shows that the current in both systems quickly declined from around 60 mA to less than 1 mA in the first hour.
Figure 8:
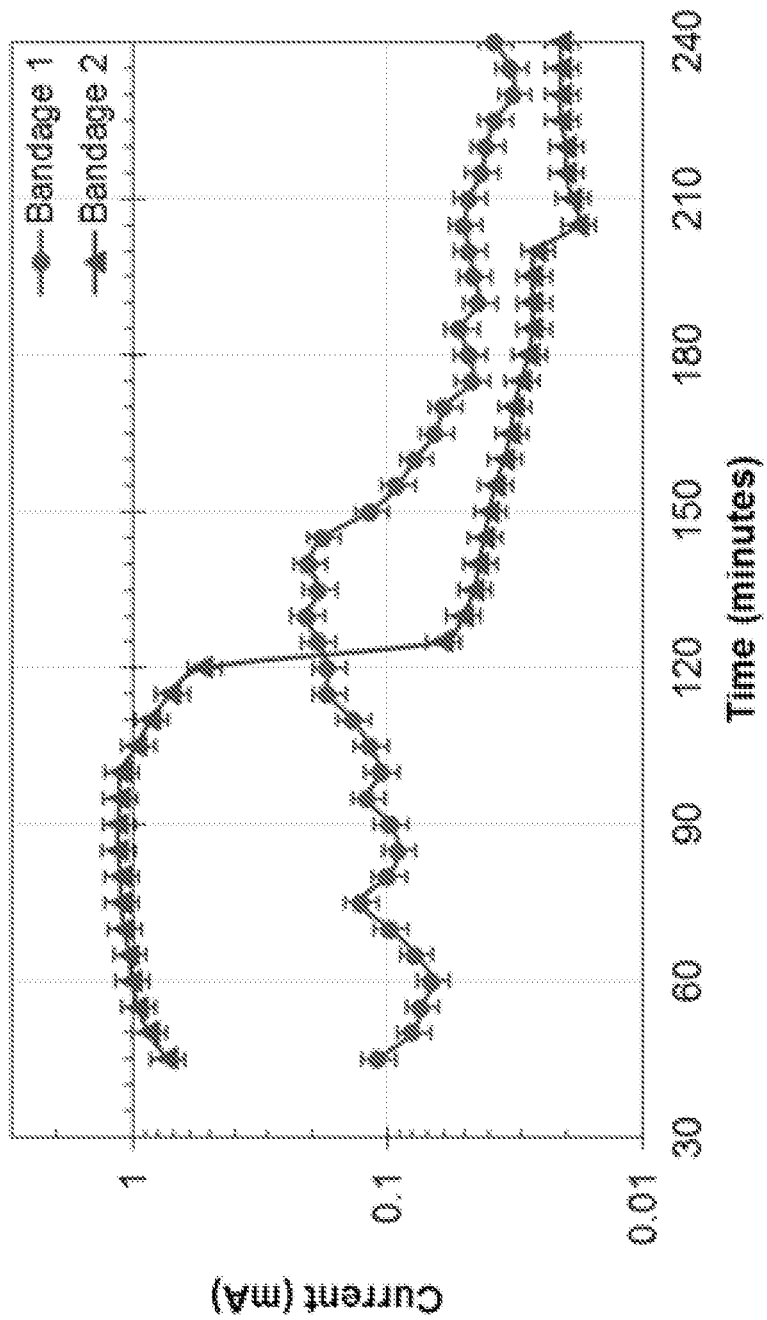
FIG. 8 is a semilogarithmic plot of in vitro current measurements with adjusted time interval to better observe the trends in current magnitude after 45 minutes.

FIG. 7 shows that the current in both systems quickly declined from around 60 mA to less than 1 mA in the first hour. Considering that the in vitro studies with bacteria were conducted for 24 hour treatment durations, this discovery was surprising. Within the first hour or data collection, similar trends were observed between the two bandages. An initial steep decline in current occurred in the first ten minutes, followed by a steadier decline over the next 15-20 minutes. This was again followed by a sharp decline down to magnitudes below 1 mA. To better observe the trends after one hour of testing, a separate plot was created for the time interval from 45 minutes to 240 minutes (see FIG. 8). FIG. 8 is a semilogarithmic plot of in vitro current measurements with adjusted time interval to better observe the trends in current magnitude after 45 minutes.

In summary of the recorded current measurements, maximum, minimum, and average currents were determined (Table I, below). From these values, current density was calculated using the areas of the anode and cathode mentioned earlier. The maximum current density (see Table 2) of the system in either of the two bandage cases was 29.07 mA/cm², which occurred at the cathode. The minimum current density of 0.0006 mA/cm² was achieved at the anode.

TABLE 1

Summary of current data collected, including maximum, minimum and average current magnitudes of the two bandages.

| Maximum Current (mA) | Average Current (mA) | Minimum Current (mA) |
|---|---|---|
| 65.4 | 5.044 | 0.018 |

TABLE 2

Calculated current density results using the respective cathode and anode areas of 2.25 cm² and 31.50 cm².

| | Maximum Current Density (mA/cm²) | Average Current Density (mA/cm²) | Minimum Current Density (mA/cm²) |
|---|---|---|---|
| Anode | 2.0762 | 0.1601 | 0.0006 |
| Cathode | 29.0667 | 2.2417 | 0.0080 |

Power density was calculated using the minimum, maximum, and average currents that occurred throughout testing, assuming that the applied voltage was 6V (Table 3). From these results, it was confirmed that the power density remained below the FDA limit on power density for thermal burns of 0.25 W/cm². The maximum power density that occurred in the system was 0.1744 W/cm² at the cathode, however the average at the cathode was well below the threshold at 0.0135 W/cm².

TABLE 3

Calculated power densities using the maximum, average, and minimum current magnitude results and an applied potential of 6 V.

| | Maximum Power Density (W/cm²) | Average Power Density (W/cm²) | Minimum Power Density (W/cm²) |
|---|---|---|---|
| Anode | 0.01246 | 0.00096 | 0.00000 |
| Cathode | 0.17440 | 0.01345 | 0.00005 |

Throughout current measurements, a few key observations were noted. The first was bubbling in the agar at the cathode. The second observation was condensation on the lid of the petri dish directly above the conductive pattern only.

These observations suggested electrolysis occurred in the agar. Another study reported on occurrence of hydrolysis and it was believed that the generation of hypochlorous acid at the anode killed the biofilm bacteria (Sandvik, E. L., McLeod, B. R., Parker, A. E., & Stewart, P. S. (2013). Direct electric current treatment under physiologic saline conditions kills *Staphylococcus epidermidis* biofilms via electrolytic generation of hypochlorous acid. [Research Support, Non-U.S. Gov't]. PLOS ONE, 8(2), e55118. doi: 10.1371/journal.pone.0055118). In their study, a saline solution was used, however in this study tryptic soy agar was used. However, both solutions contained sodium chloride. The composition of tryptic soy agar (pH 7.3±0.2) is shown in Table 4.

TABLE 4

Composition of tryptic soy agar.

| Compound | Amount (g) |
|---|---|
| Tryptone | 15 |
| Soytone | 5 |
| NaCl | 5 |
| Agar | 15 |

Throughout current measurements, a few key observations were noted. The first was bubbling in the agar at the cathode. The second observation was condensation on the lid of the petri dish directly above the conductive pattern only.

Given the presence of sodium chloride in the agar, electrolysis reactions were suspected. The electrolytic half-reactions of sodium chloride are shown below in Eq. 1 and 2. From these expressions, it is shown that chlorine gas is generated at the anode.

$$2H_2O_{(l)}+2e^- \rightarrow H_{2(g)}+2OH^-_{(aq)} \text{(cathode)} \quad (1)$$

$$2Cl^-_{(aq)} \rightarrow Cl_{2(g)}+2e^- \text{(anode)} \quad (2)$$

If chlorine gas is generated in the presence of water, hypochlorous acid and hypochlorite form (Sandvik, et al., 2013). The reaction equations for these processes are shown in Eq. 3 and 4.

$$Cl_{2(g)}+H_2O_{(l)} \rightarrow Cl^-_{(aq)}+HOCl_{(aq)}+H^+_{(aq)} \quad (3)$$

$$HOCl_{(aq)} \rightarrow H^+_{(aq)}+OCl^-_{(aq)} \quad (4)$$

Since chlorine gas was generated at the anode, hypochlorous acid and hypochlorite free chlorine compounds were also present at the anode according to the previous reaction equations. The overall electrolysis reaction equation is shown in Eq. 5.

$$H_2O_{(l)} + Cl^-_{(aq)} \rightarrow H_{2(g)} + OCl^-_{(aq)} \tag{5}$$

Therefore, the generation of free chlorine compounds such as hypochlorous acid, a known disinfectant, at the anode may explain the improved clearance observed compared to that occurring at the cathode. However, current likely also has a bacteria clearance effect and enables electrolysis to occur in the system.

Spotted Bacteria Results

The large positive electrode dressing design were further studied using in vitro tests with *Pseudomonas aeruginosa* (PA01). In these tests, around 50-75 mL of autoclaved tryptic soy agar was deposited in a 120 mm dish to evenly coat the bottom surface. After the agar set, the dressing was placed on top of the agar surface with the silk side facing upward. Another 100 mL of tryptic soy agar was poured over the dressings to fully embed them in agar. After the agar was set, 1 mL inoculated PA01 bacteria was spread onto the agar surface. At this point, the battery packs were attached to the dressings and switches turned on to start in vitro testing. The treatment was conducted in an incubator for 24 hours at 37° C.

Figure 9:
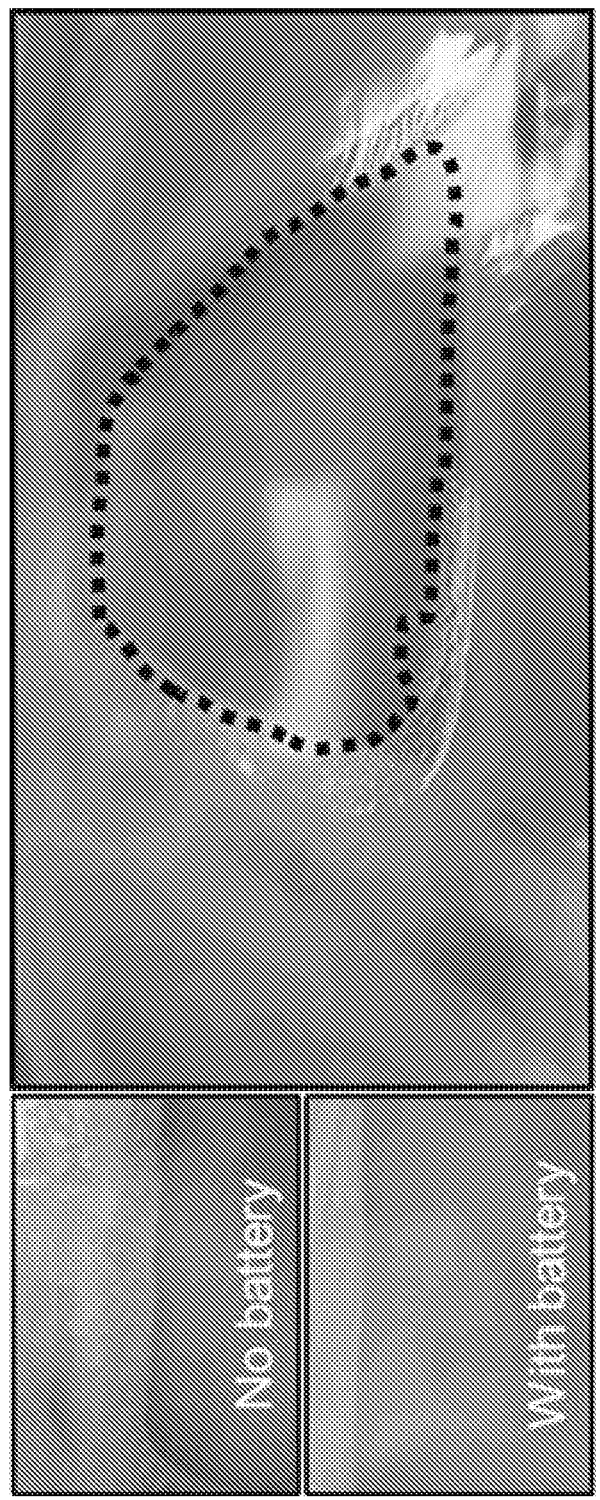
FIG. 9 is an image displaying the clearance zone of bacteria over the anode.
Figure 10:
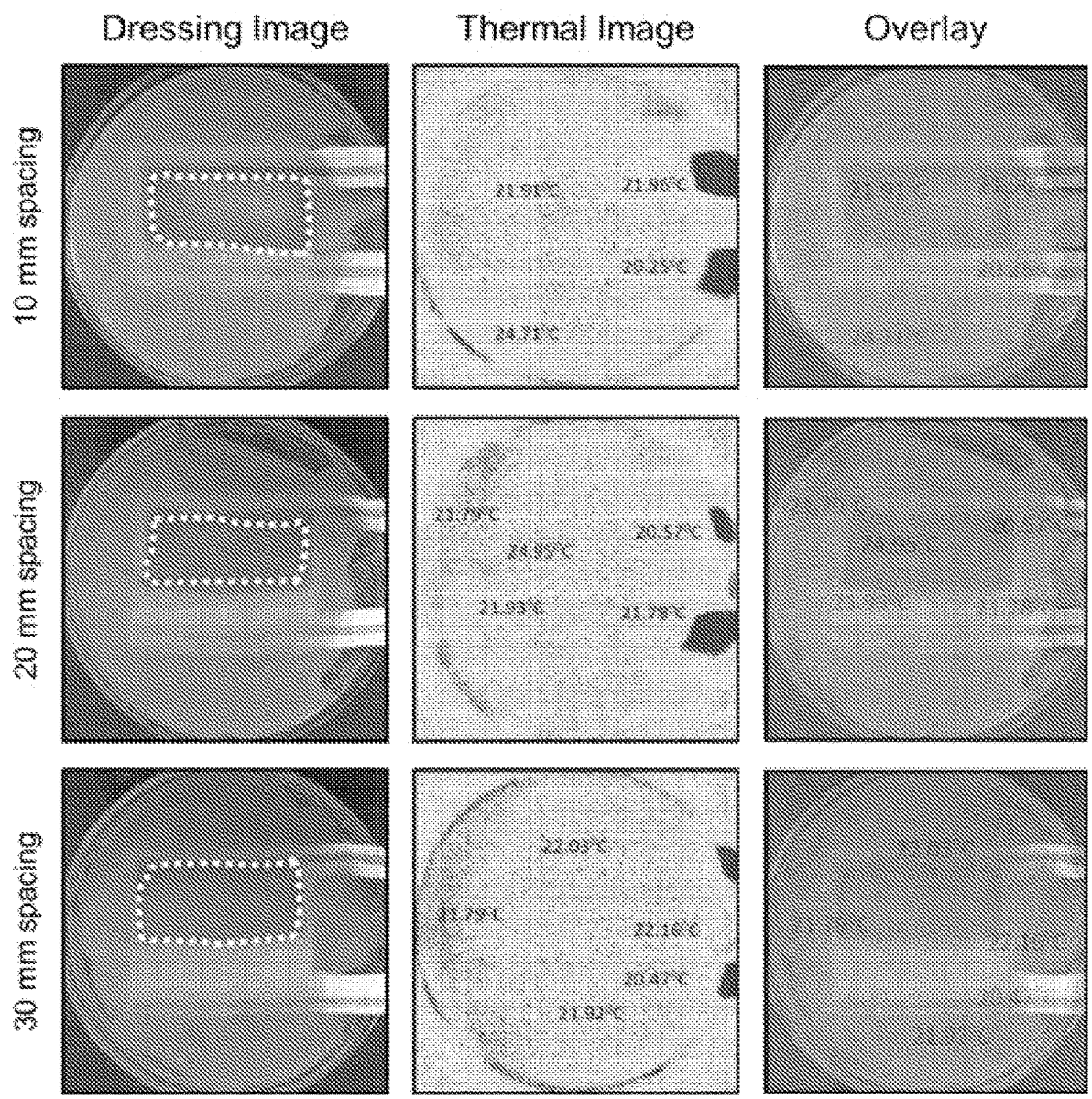
FIG. 10 shows in vitro results of three example cases presented where one dressing of each electrode spacing is shown for comparison (left) where the bacteria clearance is outlined in white dotted lines where thermal IR images are shown of the plate profile (center) and overlays of the dressing images and thermal IR images are included (right)

Testing was conducted with large positive electrode dressings of varying electrode spacing (10, 20, and 30 mm). Similar to previous design testing, bacteria clearance was much more prominent near the anode than near the cathode. An image displaying the clearance zone of bacteria over the anode is shown in FIG. 9. Which shows exclusion of bacteria observed over the anode in each case, as enclosed in dotted black lines in this example image. Notice the clear smooth region inside the dotted line, and the grainy and cloudy texture outside the dotted line. To further support the hypothesis that direct electric current was responsible for some of the bacteria exclusion, thermal IR images were captured of the Petri dishes and overlaid with the bacteria exclusion images (see FIG. 10). The thermal IR images were captured in a room temperature environment, and hence the plate does not show any local heating that suggested exclusion of bacteria through exposure to heat. FIG. 10 shows in vitro results of three example cases presented. One dressing of each electrode spacing is shown for comparison (left) where the bacteria clearance is outlined in white dotted lines. Thermal IR images are shown of the plate profile (center) and overlays of the dressing images and thermal IR images are included (right). Therefore from these studies, it was determined that the thermal effects could be ruled out as the mode for bacteria clearance.

Figure 11:
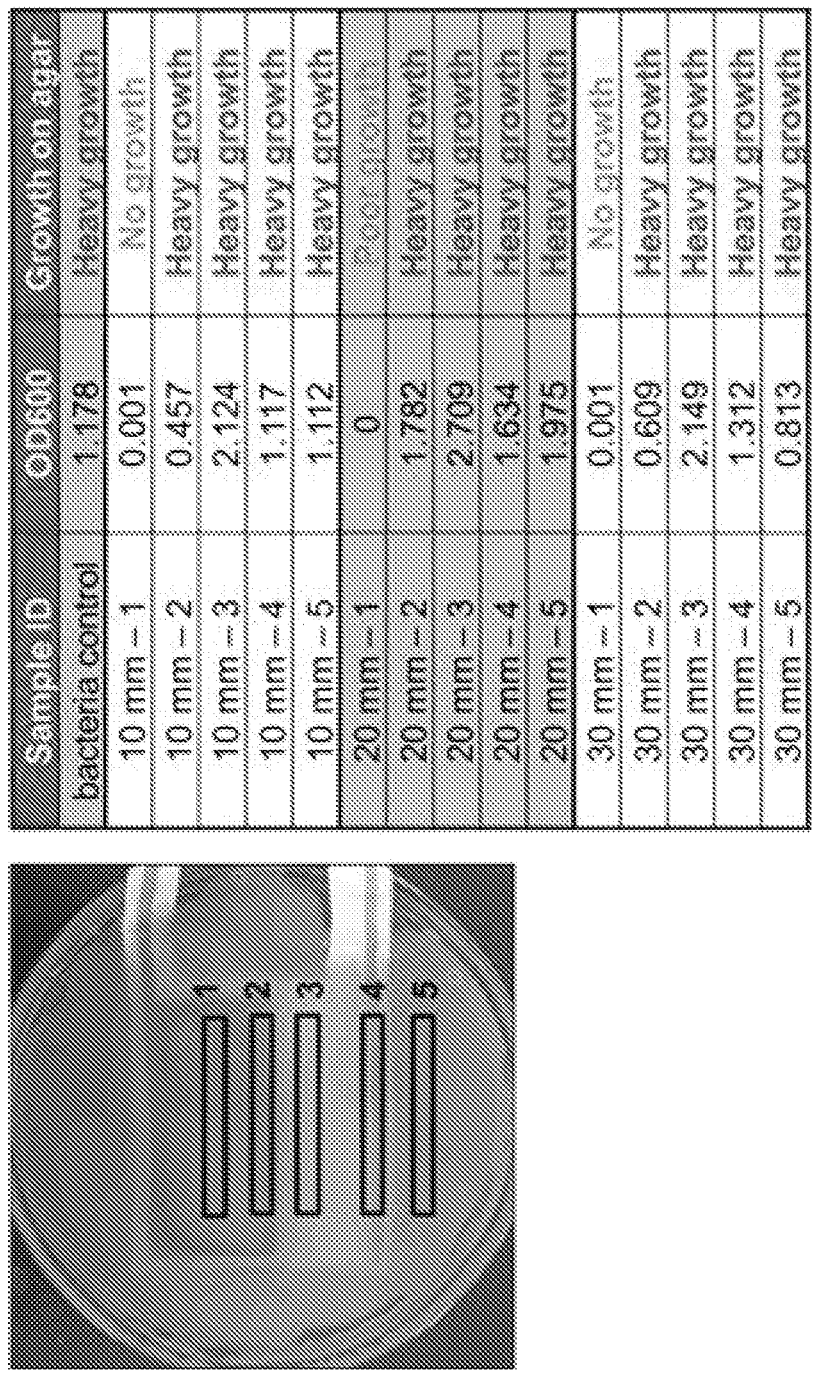
FIG. 11 shows where swabs were taken from five locations within the dishes to quantify the amount of bacteria clearance.

To quantify the amount of bacteria clearance, swabs were taken from five locations within the dishes, as indicated by FIG. 11 FIG. 11 shows quantified bacteria growth by log colony forming units (CFUs) from five regions of the surface of the agar and bacteria. Three representative cases presented, one from each electrode spacing design (10, 20, and 30 mm). The first swab was collected from the center region of the anode, the second from the border of the anode closest to the cathode, the third from the region between the anode and cathode, the fourth from the cathode, and the fifth from the region beyond the cathode and dressing. The swabs collected from this test are plated and measured for viability of growth from the swab of bacteria. FIG. 11 shows quantified bacteria growth by log colony forming units (CFUs) from five regions of the surface of the agar and bacteria. Three representative cases presented, one from each electrode spacing design (10, 20, and 30 mm).

Referring to FIG. 11, the resulting log colony forming unit (CFU) data confirmed that bacteria had little to no growth over the anode (region 1), as observed throughout testing. Region 2 had less growth than the remaining regions in the 10 mm and 30 mm spacing cases. In all cases, region 3 showed the greatest growth, contrary to the expectation that region 5 beyond the dressing would have the most growth due to lack of treatment in that zone. However, after reviewing these results, it was concluded that the area toward the edge of the plate probably has a less dense population of bacteria when it is deposited onto the agar surface before treatment. It seemed reasonable that the center of the bacteria colony would thrive because the bacteria were more shielded from the environment than those at the edges of the colony.

One last bacteria quantification analysis was performed to further support the bacteria growth results seen thus far. Live/dead staining yielded images that were later quantified for amount of living bacteria compared to amount of dead bacteria. The stain used for this study was LIVE/DEAD BacLight Bacterial Viability Kit, including SYTO® 9 green-fluorescent nucleic acid stain and red-fluorescent nucleic acid stain, propidium iodide. These stains differ in their spectral characteristics, but also in their ability to penetrate bacterial cells. The "live" stain reacts with intact cell membranes and fluoresces green, while the "dead" stain reacts with damaged membranes and fluoresces red. This provided a great representation of the bacteria behavior over the anode.

Figure 12:
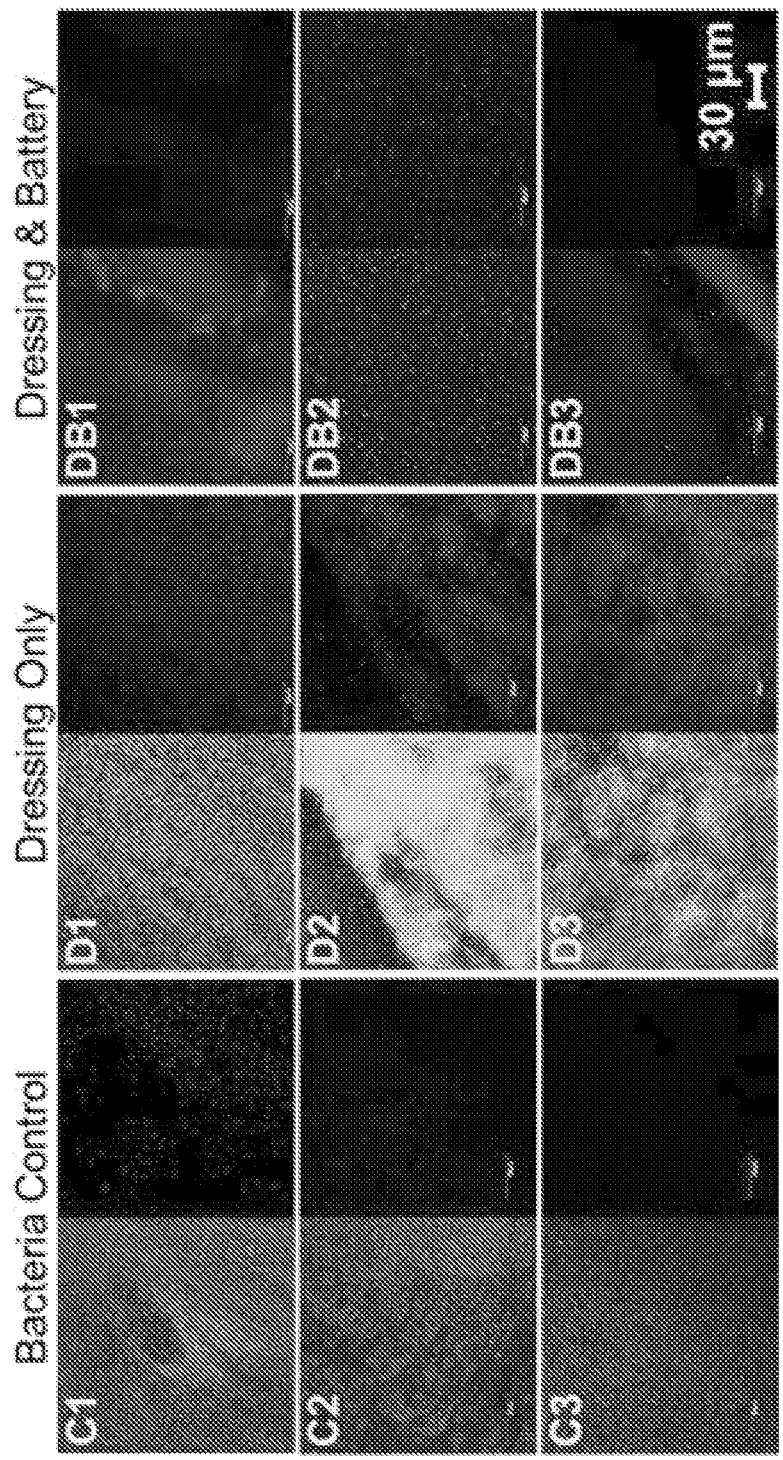
FIG. 12 shows the live/dead staining results from the three cases: bacteria control (left), dressing only treatment (middle), and dressing and battery with direct current treatment (right)

In this study three cases were conducted: (i) bacteria control with no treatment applied, (ii) a dressing only case with an embedded dressing but no connection to power, and (iii) a dressing and battery case with an active direct current treatment. In each case, three different images were analyzed, each from a different dressing. The images were taken from the area above the anode in every case. The resulting images from this study are shown in FIG. 12. Each sample tested was separated into two images, one with the fluorescent live bacteria and the other with the dead bacteria. FIG. 12 shows the live/dead staining results from the three cases: bacteria control (left), dressing only treatment (middle), and dressing and battery with direct current treatment (right). Images were sampled from the area above the anode for three different bandages in each case.

From the live/dead staining images, it was apparent that the control had a moderate amount of living bacteria, and very few dead bacteria. However, the dressing only case appeared to have a very dense population of living bacteria, and a moderate amount of dead bacteria. Lastly, the direct current treatment case visually had the fewest living bacteria and a small amount of dead bacteria. This was perplexing because although the dressing and battery case had the least amount of living bacteria, as expected, it also appeared to not indicate dead bacteria. Before conclusions were drawn, the live/dead images were processed and quantified using ImageJ to filter and count the pixels of either green or red color. The resulting quantified data is shown in FIG. 13.

The quantified results showed similar trends to the raw live/dead staining images, where the dressing only case demonstrated the largest amount of both living and dead bacteria. Furthermore, the dressing and batter case utilizing direct current treatment showed the least amount of living bacteria by far, and very little dead bacteria. The conclusion made was that the dressing only case had the most bacteria because the dressings used for testing had been open to atmosphere during fabrication. Therefore various spores and bacteria had the ability to adhere to the dressing during this timeframe. However, the bacteria control only contains *Pseudomonas aeruginosa* deposited onto the agar during testing, as control in the lab. Furthermore, the dressing only cases exhibited the greatest amount of dead bacteria, which was most likely due to the presence of silver ink alone. Silver is known to have bactericidal properties, and therefore excludes some bacteria without the presence of direct electric current.

The conclusion drawn from the dressing and battery treatment was that the presence of direct current was forcing the cell membranes to burst or explode, spilling DNA contents. Therefore the cell membranes were not just damaged but destroyed, and unable to be detected by the dead bacteria stain. The live/dead results are summarized FIG. 14, which shows the summary of results from quantification of living and dead bacteria for each of the three cases. The values reported were based on the average results from the three trials in each case.

Figures 13, 14:
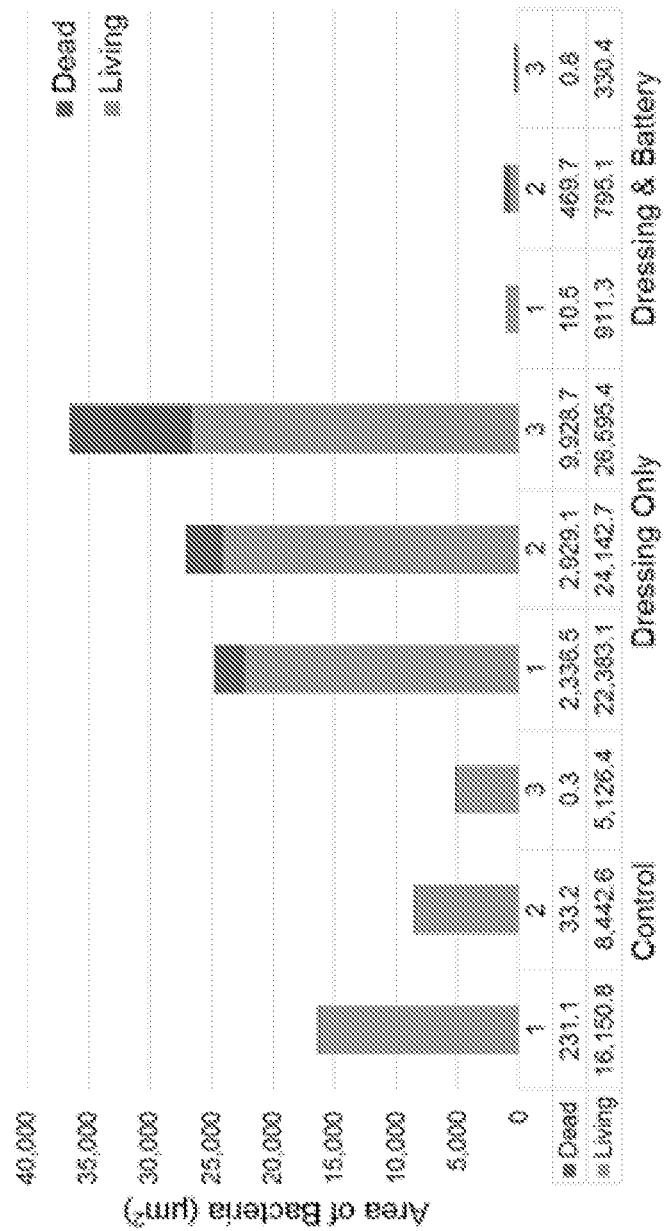
FIG. 13 shows the quantified data after the live/dead images were processed and quantified using ImageJ to filter and count the pixels of either green or red color.
FIG. 14 shows the summary of results from quantification of living and dead bacteria for each of the three cases.

From FIG. 14, the average areas of live and dead to not total to equal one hundred percent of the area observed. This occurred due to either empty space that contained neither live or dead bacteria, resulting in a total less than one hundred percent, or live and dead bacteria were stacked on top of each other, and therefore occupying the same space in a 2D image.

In summary, the results presented throughout this section showed that the silver/silver chloride and silk bandage prevented biofilm formation of PA01, as evidenced by the observed bacteria clearance and lack of pyocyanin production.

Excised Pre-Formed Biofilm Results

Figure 15:
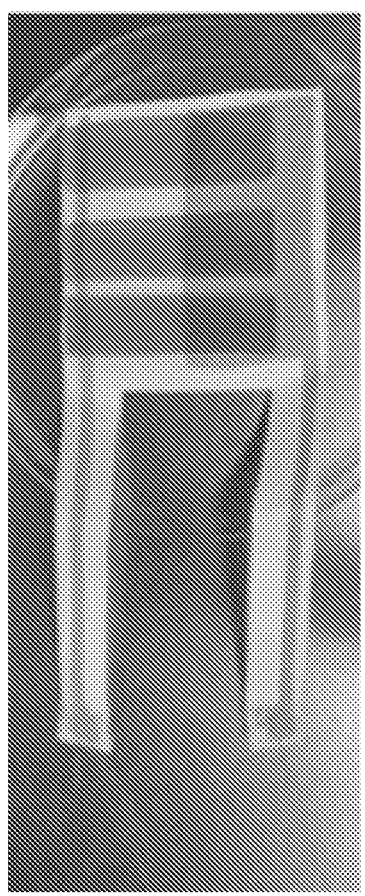
FIG. 15 shows pre-formed biofilm in vitro testing setup with strips of tryptic soy agar with pre-grown PA01 biofilms where the strips appeared green due to the pyocyanin production in the biofilm.

In this final study, PA01 biofilms were grown for 24 and 48 hours on tryptic soy agar prior to testing. Strips were then cut out of the dish and placed over the bandage, connecting the anode to the cathode, as demonstrated in FIG. 15. Each bandage was then connected to a 6V battery pack like the previous tests, and treatment continued for 24 hours in an incubator at 37° C. FIG. 15 shows pre-formed biofilm in vitro testing setup with strips of tryptic soy agar with pre-grown PA01 biofilms. The strips appeared green due to the pyocyanin production in the biofilm.

Figure 16:
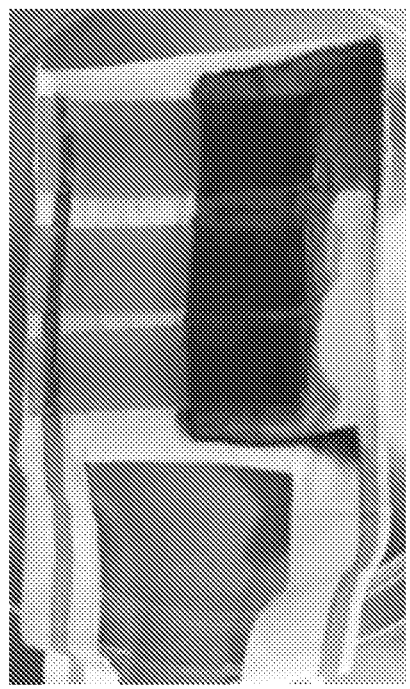
FIG. 16 shows the bandages of FIG. 15 that were connected to batteries showing leaching of silver and the agar strips were dehydrated.

After the 24 hour testing duration, the dishes were removed from the incubator and a few key observations were noted. The bandages connected to batteries showed leaching of silver and the agar strips were dehydrated (see FIG. 16). It was suspected that the magnitude of current was too large in this system causing reactions to take place at the anode and leaching of silver. Although the applied voltage remained the same compared to other cases, the volume of agar present in the system was less, thereby lowering the resistance of the system and increasing the current. Therefore, in future studies of this method and future designs of the bandage, resistors should be included to limit current.

Figure 17:
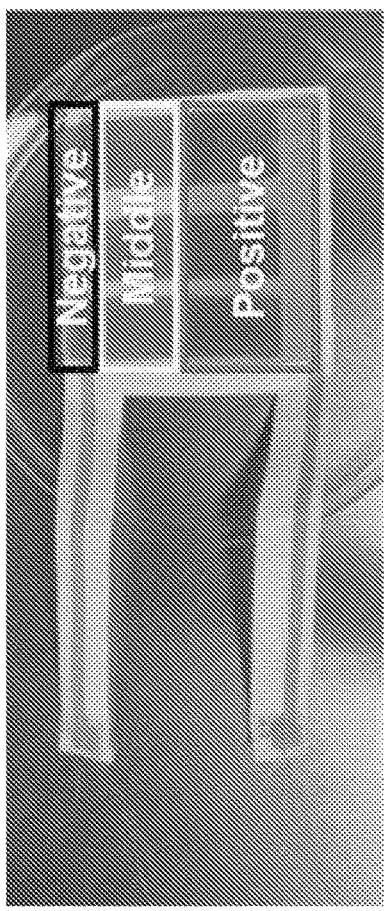
FIG. 17 shows punch biopsies were collected from three regions (i) positive electrode, (ii) middle region, and (iii) negative electrode.

However, the pre-formed biofilm results were still tested and bacteria growth was quantified by collecting punch biopsy samples from the agar strips and analyzing them for bacteria growth. Punch biopsies were collected from three regions (i) positive electrode, (ii) middle region, and (iii) negative electrode, as shown in FIG. 17.

Figure 18:
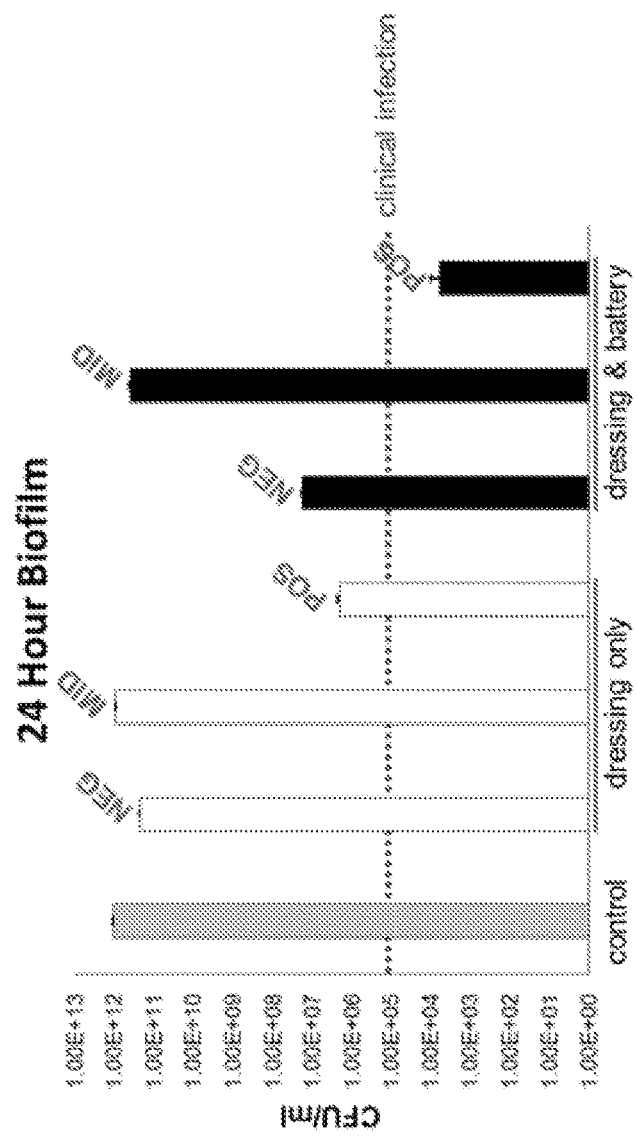
FIG. 18 presents the 24 hour pre-grown biofilm results.
Figure 19:
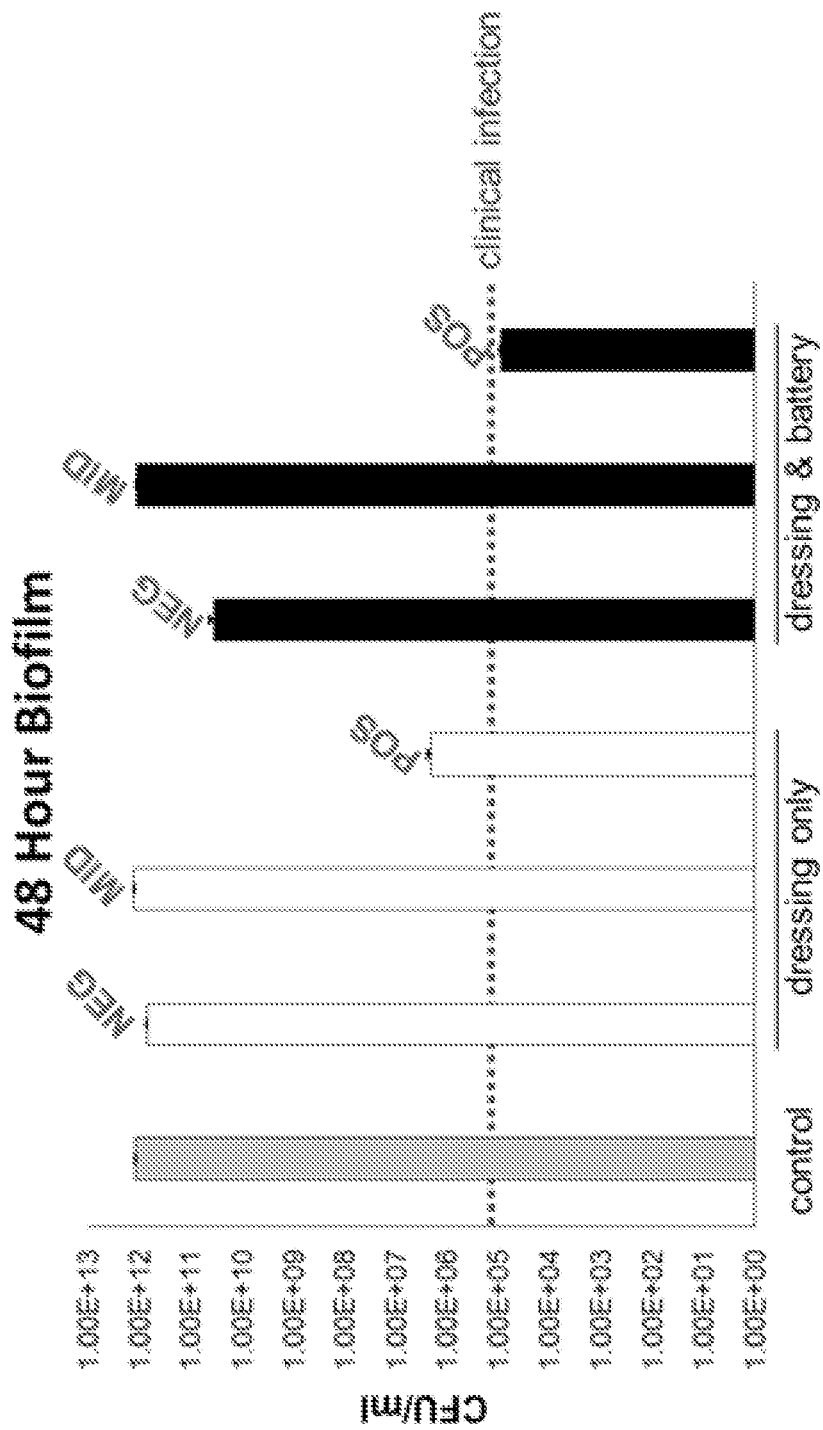
FIG. 19 presents that of the 48 hour biofilm.

For this study, once again three cases were conducted: (i) bacteria control without any treatment, (ii) dressing only with no connection to battery, and (iii) dressing and battery treatment with direct electric current. In cases (ii) and (iii), punch biopsies were collected from the three regions described in FIG. 17. The biopsies were quantified for growth viability and the results are reported in the two following plots, where FIG. 18 presents the 24 hour pre-grown biofilm results. FIG. 19 presents that of the 48 hour biofilm. FIG. 18 shows bacteria growth viability results from a 24 hour treatment test using the large positive electrode bandage and strips of 24 hour pre-grown PA01 biofilm on tryptic soy agar. FIG. 19 shows Bacteria growth viability results from a 24 hour treatment test using the large positive electrode bandage and strips of 48 hour pre-grown PA01 biofilm on tryptic soy agar. Each bar plotted in the graphs of FIGS. 18 and 19 represented an average value of three samples and error bars are shown.

The resulting bacteria growth viability plots indicate that the control had a large amount of growth at around $1\times10^{12}$ CFU/mL. In both the 24 and 48 hour pre-grown biofilm cases, the results for both the no battery and with battery cases from the middle region between the cathode and anode had growth similar to that of the control. However, there are significant differences between the negative and positive samples of the no battery and battery cases. For instance, the negative electrode with current flow showed improved bacteria clearance compared to that with just the dressing in both the 24 and 48 hour cases.

When the positive electrode sample results were compared, it appeared that in all cases (with and without batter, 24 and 48 hour) the positive electrode samples exhibited the worst growth. However, the only cases that reduced the biofilm enough to be considered less than the clinical threshold of infection ($1\times10^5$ CFU/mL) were the positive electrode samples taken from the dressings connected to 6V battery packs. The 24 and 48 hour results show similar trends across the board, except that the 48 hour biofilm exhibited slightly more growth from the punch biopsy samples. This was expected because the 48 hour biofilms were most established, sturdier biofilm structures.

In conclusion, the large positive electrode design bandages were able to successfully diminish pre-formed biofilms near the anode to growth levels below the clinical infection threshold. However, heavy growth was still achieved near the cathode and area in between the anode and cathode.

Proposed Alternate Designs

After observations throughout testing, some design modifications were made to address a few issues. First, leaching of silver was observed throughout most in vitro studies conducted in this project. There were various solutions considered to resolve this issue, including use of silver foil, sputtering a silver pattern onto silk Habotai, and flash evaporation of silver foil. However, it the hypothesis of the leaching was determined to be a direct result of a large magnitude of current inducing reactions in the media and at the electrodes. Therefore, it was determined that resistors should be added in series with the bandage and battery pack to limit the current in the system. Furthermore, an LED could be included in the circuit to serve as a visual cue for the user that the battery pack is connected and the bandage is operational.

Figure 20:
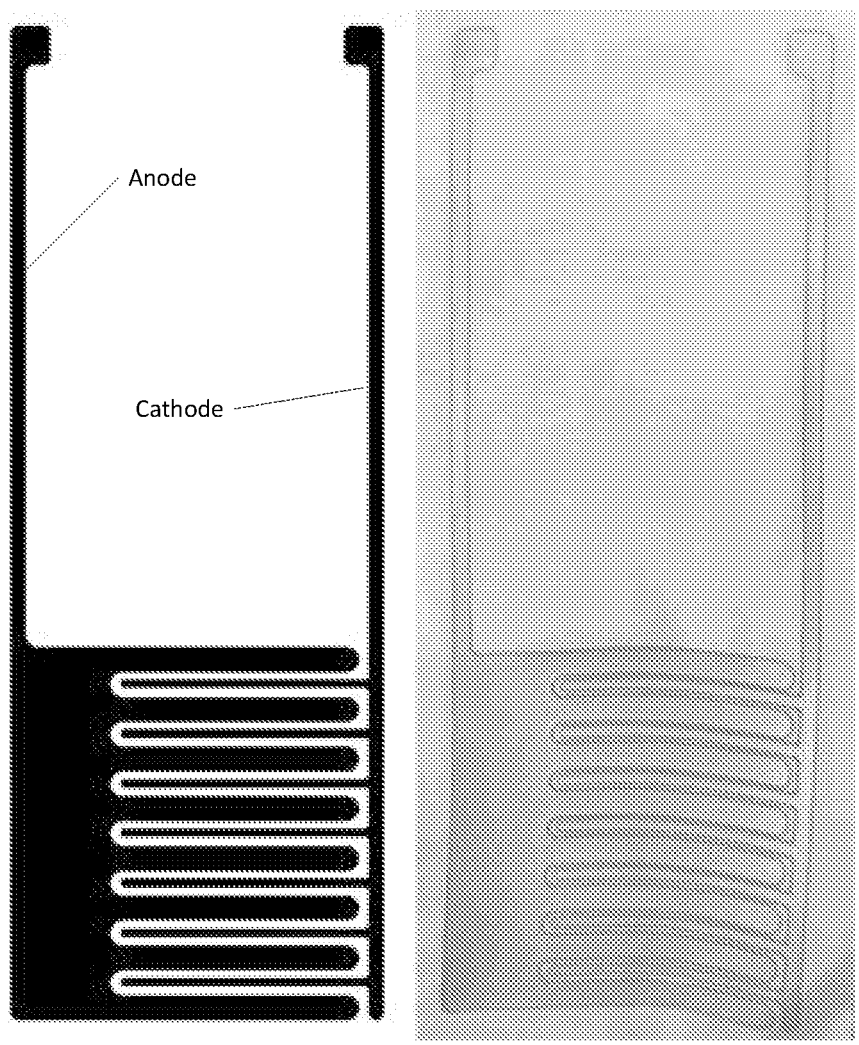
FIG. 20 shows a comb pattern design for the anode and cathode to treat a larger area of biofilm.

Second, clearance of bacteria was predominantly observed and quantified over the anode, with little impact over the cathode or unprinted areas. To address this observation, the electrode design was further modified toward a comb pattern design that covers nearly the entire active area of the dressing. This design is shown in FIG. 20, which shows a comb pattern design for the anode and cathode to treat a larger area of biofilm. This electrode pattern features interlocking teeth-like pattern of positive and negative electrodes. This design is still an open circuit design, however there is a much smaller gap between electrodes.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications may be referenced. The disclosures of these publications in their entireties are hereby incorporated by reference into this application in order to more fully describe the state of the art to which the methods and systems pertain and to illustrate improvements over the present state of the art in claimed invention.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not target to be exhaustive or to limit the embodiments to the precise forms disclosed. It will be apparent to one of ordinary skill in the art that many modifications and variations are possible in view of the above teachings.

What is claimed is:

1. A method of treating a bacterial infection in a wound, the method comprising:
    applying an antimicrobial dressing to the wound, said antimicrobial dressing comprising:
        a substrate;
        at least one pair of electrodes positioned on or within the substrate, wherein the at least pair of electrodes comprise a conductive anode configured to be in contact with at least a first portion of the wound and a conductive cathode configured to be in contact with at least a second portion of the wound; and
        a plurality of electrodes in a spaced pattern on the substrate, wherein at least a portion of the plurality of electrodes in the spaced pattern are configured to be in contact with the wound;
    inducing, by an energy source configured to be connected to the at least one pair of electrodes, an electrical current to flow from the conductive anode, through the wound, to the conductive cathode, wherein the energy source configured to be connected to the at least one pair of electrodes comprises the portion of the plurality of electrodes in the spaced pattern on the substrate that are configured to be in contact with the wound, a first subset of the plurality of electrodes connected in electrical series with the anode and a second set of the plurality of electrodes connected in electrical series with the cathode, and the plurality of electrodes are comprised of a biocompatible reduction/oxidation reaction material such that a voltage differential is created between the anode and the cathode, wherein said voltage differential causes the electrical current to flow from the conductive anode, through the wound, to the conductive cathode; and
    applying a therapeutically effective amount of an electric current to the wound from the antimicrobial dressing.

2. The method of claim 1, wherein the electrical current flowing through the wound inhibits formation of a biofilm within the wound, at least partially disrupts a biofilm growing within the wound, at least partially destroys sessile bacteria within the wound, and/or at least partially destroys planktonic bacteria within the wound or disrupts bacterial growth in the wound or inhibits or disrupts biofilm in the wound.

3. The method of claim 2, wherein the biofilm comprises sessile bacteria that are resistant to antibiotics.

4. A method of assembling an antimicrobial dressing, comprising:
    applying a layer of conductive material to an insulated base substrate to form at least one electrode pair on the insulated base substrate, wherein the electrode pair comprise a conductive anode and a conductive cathode that are electrically insulated from one another,
    connecting an energy source to the at least one electrode pair, wherein the energy source induces an electrical current to flow from the conductive anode, through a wound, to the conductive cathode; and
    forming a plurality of electrodes in a spaced pattern on the substrate, wherein at least a portion of the plurality of electrodes in the spaced pattern are configured to be in contact with the wound, and wherein the energy source connected to the at least one electrode pair comprises the portion of the plurality of electrodes in a spaced pattern on the substrate that are configured to be in contact with the wound, a first subset of the plurality of electrodes connected in electrical series with the anode and a second set of the plurality of electrodes connected in electrical series with the cathode, and the plurality of electrodes are comprised of a biocompatible reduction/oxidation reaction material such that a voltage differential is created between the anode and the cathode, wherein said voltage differential causes the electrical current to flow from the conductive anode, through the wound, to the conductive cathode.

5. The method of claim 4, wherein applying the layer of conductive material to the insulated base substrate to form the at least one electrode pair on the insulated base substrate comprises printing the conductive anode and the conductive cathode on the substrate using screen-printing techniques or printing the conductive anode and the conductive cathode on the insulated base substrate using a printer.

6. The method of claim 4, wherein applying the layer of conductive material to the insulated base substrate to form the at least one electrode pair on the insulated base substrate comprises weaving the conductive anode and the conductive cathode into the insulated base substrate.

* * * * *